US011660071B2

(12) United States Patent
Yang et al.

(10) Patent No.: US 11,660,071 B2
(45) Date of Patent: May 30, 2023

(54) RADIAL ARRAY TRANSDUCER-BASED PHOTOACOUSTIC AND ULTRASONIC ENDOSCOPY SYSTEM

(71) Applicant: UNIST(ULSAN NATIONAL INSTITUTE OF SCIENCE AND TECHNOLOGY), Ulsan (KR)

(72) Inventors: Joon Mo Yang, Ulsan (KR); Chae Un Kim, Ulsan (KR)

(73) Assignee: UNIST(ULSAN NATIONAL INSTITUTE OF SCIENCE AND TECHNOLOGY), Ulsan (KR)

( * ) Notice: Subject to any disclaimer, the term of this patent is extended or adjusted under 35 U.S.C. 154(b) by 138 days.

(21) Appl. No.: 16/127,097

(22) Filed: Sep. 10, 2018

(65) Prior Publication Data

US 2019/0076119 A1 Mar. 14, 2019

(30) Foreign Application Priority Data

Sep. 11, 2017 (KR) ........................ 10-2017-0115911

(51) Int. Cl.
*A61B 8/00* (2006.01)
*G02F 1/29* (2006.01)
(Continued)

(52) U.S. Cl.
CPC .............. *A61B 8/4416* (2013.01); *A61B 1/07* (2013.01); *A61B 5/0035* (2013.01); *A61B 5/0095* (2013.01); *A61B 5/42* (2013.01); *A61B 8/12* (2013.01); *A61B 8/4483* (2013.01); *A61B 8/4494* (2013.01); *B06B 1/0622* (2013.01); *G02F 1/29* (2013.01); *H10N 30/87* (2023.02);
(Continued)

(58) Field of Classification Search
CPC ... A61B 8/4416; A61B 8/4483; A61B 5/0095; A61B 8/12; G01N 29/2418
See application file for complete search history.

(56) References Cited

U.S. PATENT DOCUMENTS 4,543,960 A 10/1985 Hauri et al.
4,982,724 A 1/1991 Saito et al.
(Continued)

FOREIGN PATENT DOCUMENTS

CN 101912250 12/2010
JP 2006212077 8/2006
(Continued)

OTHER PUBLICATIONS

Tsyboulski et al., "Dual modality optoacoustic and laser ultrasound endoscopy system," Photons Plus Ultrasound: Imaging and Sensing 2014, vol. 8943, Mar. 2014, (p. 1-6) (Year: 2014).*
(Continued)

*Primary Examiner* — Bill Thomson
*Assistant Examiner* — Aminah Asghar
(74) *Attorney, Agent, or Firm* — Klarist Sparkman, LLP

(57) ABSTRACT

A photoacoustic and ultrasonic endoscope includes an optical fiber, a light diffuser configured to radially diffuse a laser beam transmitted through the optical fiber, and an array transducer having a cylindrical shape and surrounding the light diffuser, the array transducer being configured to transmit the diffused laser beam therethrough and to generate an ultrasonic wave or detect an ultrasonic wave generated by an object to be examined.

15 Claims, 27 Drawing Sheets

(51) Int. Cl.
*A61B 5/00* (2006.01)
*A61B 1/07* (2006.01)
*A61B 8/12* (2006.01)
*B06B 1/06* (2006.01)
*H10N 30/87* (2023.01)
*H10N 39/00* (2023.01)

(52) U.S. Cl.
CPC ............ *H10N 39/00* (2023.02); *A61B 5/0044* (2013.01); *B06B 2201/76* (2013.01); *G02F 2201/02* (2013.01); *G02F 2201/34* (2013.01); *G02F 2203/03* (2013.01); *G02F 2203/28* (2013.01)

(56) References Cited

U.S. PATENT DOCUMENTS

| | | | |
|---|---|---|---|
| 5,125,411 A | 6/1992 | Yokoi et al. | |
| 5,337,381 A * | 8/1994 | Biswas | A61N 5/0601 385/128 |
| 8,758,251 B2 | 6/2014 | Kohno | |
| 8,764,666 B2 * | 7/2014 | Chen | A61B 8/4461 600/462 |
| 8,932,223 B2 | 1/2015 | Ernelianov et al. | |
| 10,095,528 B2 | 10/2018 | Suissa et al. | |
| 2002/0105250 A1 * | 8/2002 | Klee | H01L 41/319 310/365 |
| 2007/0206193 A1 * | 9/2007 | Pesach | A61B 5/0095 356/432 |
| 2008/0019657 A1 * | 1/2008 | Maitland | G02B 6/262 385/38 |
| 2009/0275839 A1 | 11/2009 | Sawada et al. | |
| 2010/0016717 A1 * | 1/2010 | Dogra | A61B 5/0095 600/437 |
| 2010/0249570 A1 * | 9/2010 | Carson | A61B 5/0095 600/407 |
| 2011/0021924 A1 | 1/2011 | Sethuraman et al. | |
| 2011/0275890 A1 * | 11/2011 | Wang | A61B 8/12 600/104 |
| 2014/0051967 A1 * | 2/2014 | Irisawa | A61B 5/0095 600/407 |
| 2014/0180055 A1 * | 6/2014 | Glynn | A61M 1/84 600/407 |
| 2015/0173626 A1 * | 6/2015 | Irisawa | A61B 8/445 600/407 |
| 2015/0208924 A1 * | 7/2015 | Li | A61B 5/0095 600/407 |
| 2017/0000353 A1 * | 1/2017 | Li | A61B 1/0615 |
| 2020/0196873 A1 * | 6/2020 | Ntziachristos | A61B 1/00147 |

FOREIGN PATENT DOCUMENTS

| | | |
|---|---|---|
| JP | 2015016020 | 1/2015 |
| KR | 10-2014-0126554 A | 10/2014 |
| SU | 1478064 A1 * | 5/1989 |

OTHER PUBLICATIONS

Yang et al.: Photoacoustic endoscopy, Optics Letters vol. 34, No. 10 (May 15, 2009), p. 1591-1593 (Year: 2009).*
Office Action for Korean Patent Application No. 10-2017-0115911, dated Jan. 21, 2019.
American National Standard for Safe Use of Lasers, Laser Institute of America (2007).
Bell et al., "Integrated transrectal probe for translational ultrasound photoacoustic imaging," *Proceedings of SPIE* (2016).
Dietrich, *Endoscopic Ultrasound: An introductory Manual and Atlas*, Therne, Stuttgart, New York, 2nd edition (2011).
Hanrath et al., "Transesophageal Horizontal and Sagittal Imaging of the Heart with a Phased Array System. Initial Clinical Results.", *Cariovascular Diagnosis by Ultrasound*, Martinus Nijhoff Publishers, The Hague (1982).
Oraevsky et al. "Laser Optoaeoustie Tomography of Layered Tissues: Signal Processing," *SPIE* vol. 2979.
Tsyboulski et al., "Dual modality optoacoustic and laser ultrasound endoscopy system," *Photons Plus Ultrasound: Imaging and Sensing 2014*.
Wygant et al., "Integrated Ultrasound Imaging Systems Based on Capacitive Micromachined Ultrasonic Transducer Arrays," *IEEE Sensors 2005*.
Yang et al., "Photoacoustic endoscopy," *Optics Letters*, vol. 34, No. 10, May 15, 2009.
Yang et al., "Simultaneous functional photoacoustic and ultrasonic endoscopy of internal organs in vivo," *Nature Medicine*, Aug. 2012.
Yuan et al., "Preclinical photoacoustic imaging endoscope based on acousto-optic coaxial system using ring transducer array," *Optical Society of America* (2010).

* cited by examiner

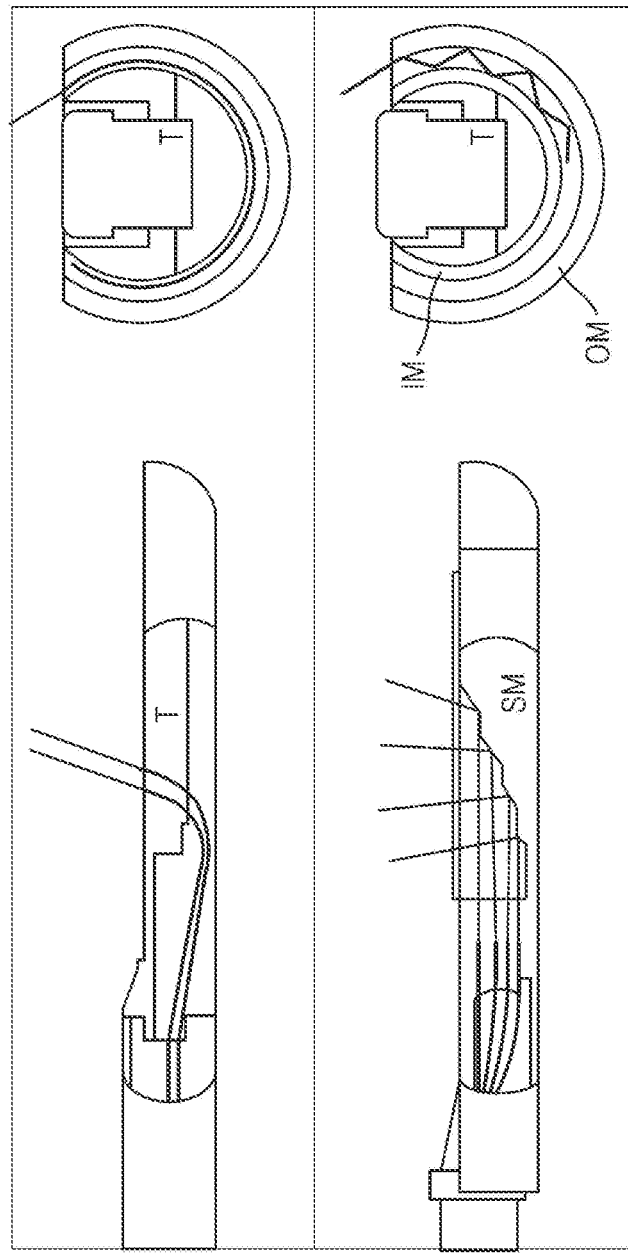
FIG. 16C PRIOR DOCUMENT 15

RADIAL ARRAY TRANSDUCER-BASED PHOTOACOUSTIC AND ULTRASONIC ENDOSCOPY SYSTEM

STATEMENT REGARDING SUPPORTED GRANT

This invention was supported by Basic Science Research Program through the National Research Foundation (NRF) of Korea funded by the Ministry of Education (2015R1D1A1A01059361), U-K Brand Research Fund (1.180016.01) of UNIST (Ulsan National Institute of Science & Technology), and Basic Science Research Program through the NRF funded by the Ministry of Science, ICT and future Planning (2014R1A2A1A11051254).

CROSS-REFERENCE TO RELATED APPLICATION

This application claims the benefit of Korean Patent Application No. 10-2017-0115911, filed on Sep. 11, 2017, in the Korean Intellectual Property Office, the disclosure of which is incorporated herein in its entirety by reference.

BACKGROUND

1. Field

One or more of the embodiments of the present disclosure relate to a medical tomographic photoacoustic-ultrasonic endoscopic apparatus that has a probe that is long and slender, like the current radial array transducer-based endoscopic ultrasound (EUS) probes utilized in clinics, wherein the endoscopic apparatus is inserted into an object to be examined and provides a tomographic image of the interior thereof.

2. Description of the Related Art

The present disclosure relates to a range of tomographic endoscopic systems that can provide cross-sectional or volumetric images of target tissue based on the general principle of photoacoustic endoscopy (PAE) or optoacoustic endoscopy (OAE) (see Prior Documents 7 and 8), and conventional EUS (see Prior Documents 1-6) by consolidating the relevant functions in a single device. The proposed endoscopic systems are intended to be used for a variety of medical procedures, such as the diagnosis of digestive diseases or cardiovascular diseases, by using an ultrasonic array transducer as the core part of the proposed systems, like the current radial array transducer-based EUS probes utilized in clinics (see Prior Documents 1-6).

The general principle of EUS is already well known and well established, and it is currently being utilized in clinical settings. However, PAE refers to the novel tomographic endoscopic technique that embodies PAT or photoacoustic imaging (PAI) technique in a small probe. In an illustrative imaging procedure, a probe with a small diameter is inserted into an object to be examined. Electromagnetic waves with a very short pulse width (usually less than 1 µs) are instantly applied to the region of interest to generate acoustic waves, which are typically referred to as photoacoustic waves, and a tomographic image of the interior of the biological tissue is produced by obtaining (i.e., scanning) the generated photoacoustic signals over the region of interest.

Although the photoacoustic effect through which electromagnetic waves are applied to a target object and converted into acoustic waves has been known since the 1880s, it was not until the early of 1990s that the first photoacoustic image was actually obtained from real biological tissue based on the photoacoustic effect. At that time, the advent of commercial pulsed-light sources, such as the Q-switched laser, played a crucial role in the breakthrough; from then on, various types of PAI systems have been developed with a greater range of medical applicability. In general, a technique that can provide a tomographic image of the interior of biological tissue based on the photoacoustic effect is referred to as PAT or PAI.

The reason that PAT is currently in the medical imaging spotlight is because it is capable of providing a new type of medically useful image information that is not possible to obtain with conventional medical imaging techniques, such as magnetic resonance imaging, X-ray computed tomography, positron emission tomography, and ultrasonography. Furthermore, it is widely accepted that PAT is very excellent, in terms of imaging depth, spatial resolution, imaging speed, and safety, all of which are critical factors for actual clinical use.

An objective of the present disclosure is to apply the PAT technique's benefits to endoscopy or minimally-invasive imaging, and more concretely, to solve many of the limitations and problems of existing array transducer-based PAE probes, such as low imaging depths and large probe size issues, thereby to more effectively apply related technology to GI endoscopy, cardiology, urology, etc.

Like more well-known or more general PAT systems (that are not limited to endoscopy), a PAE system also requires three core system elements: a light source that generates an electromagnetic pulse (typically in the visible wavelength range), an imaging probe that approaches an object to be examined and acquires a series of photoacoustic signals, and a data processor and displayer that process the acquired photoacoustic signals and provide the processed photoacoustic image to a user. However, the shape and size of the imaging probe is the most important and distinguishable technical requirement for the specific application area called "endoscopy"; the probe should be long, and its diameter should be very small or narrow (i.e., with a thickness equal to or less than a predetermined value).

After the first conceptual suggestion of PAE by Oraevsky et al. (1997), as described in Prior Document 8, in which the imaging probe was referred to as an "optoacoustic endoscope", a number of PAE probes have been developed to address technical requirements, such as "probe miniaturization" and "specifying a device configuration or operation principle for endoscopy." However, no commercially successful or clinically applicable PAE system has yet been developed that satisfies both of these technical requirements due to many underlying technical challenges. The most well-known and difficult challenge is that, in order to successfully create a working PAE probe, all the optical and acoustical elements should be effectively integrated and arranged in a small and restricted space; an adequate scanning mechanism, through which a tomographic image can be produced, should also be developed and integrated into the device.

Accordingly, the main purpose of the present disclosure is to provide a concept for an advanced PAE system or probe structure that may satisfy the aforementioned technical requirements and allow an imaging probe to be more smoothly inserted into an object to be examined and provide a photoacoustic image with much higher quality than those of prior inventions, even from a deep inside of the object to be examined.

Although there is a clear difference between the principles of PAE and EUS, in which a PAE image is produced through the unique energy transduction mechanism that converts pulsed electromagnetic waves into acoustic waves, PAE is still very closely related to conventional EUS (see Prior Document 1). This is because all of the signals required to produce a PAE image are acquired by means of acoustic waves. This means that, in some respects, a PAE device can be understood as a device in which the functions that guide and emit laser beam (or electromagnetic waves) are added to the typical system composition of a conventional EUS device. Due to these system characteristics, most PAE systems may be able to provide both a photoacoustic image and a conventional ultrasound image.

Hence, considering only the methods of ultrasound signal detection other than those that deliver and emit electromagnetic waves (e.g., a laser beam in general) to an object to be examined, any of the single-element ultrasonic transducer-based mechanical scanning mechanisms or array transducer-based electronic scanning mechanisms currently being utilized in clinical EUS instruments may also be utilized in a PAE probe (see Prior Document 1). The advantages and disadvantages of the mechanical and the electronic scanning mechanisms are briefly explained.

First, the main advantage of the single-element ultrasonic transducer-based mechanical scanning mechanism is that it may be possible to fabricate a very small or slender-shaped probe because the space occupied by the single transducer is not very large. Moreover, the costs for implementing the related instruments are relatively low. However, the main drawback of the mechanical scanning mechanism is that, since a single-element ultrasonic transducer that can receive the signals that are bounced back only from the aiming direction of the transducer surface is mounted on the scanning tip of an endoscopic probe, in order to obtain a 2D image or a 3D image, a series of processes that emit a laser pulse, and then detect the generated photoacoustic waves, should be repeatedly performed by changing the physical position or the aiming direction of the ultrasonic transducer (e.g., rotational scanning in general). Due to the aforementioned advantages and disadvantages, in the current EUS technology utilized in clinics, the mechanical scanning mechanism is mostly applied to ultra-small endoscopic devices with probe diameters ranging from ~1 mm to ~3 mm, such as intravascular ultrasound (IVUS) catheter probes, which are manufactured for introduction into blood vessels, or EUS mini-probes, which are manufactured to be inserted into the instrument channels or the accessory channels of a video endoscope (of course, an EUS instrument does not require a laser pulse guiding and emitting function).

In contrast, the array transducer-based electronic scanning mechanism differs from the mechanical scanning mechanism in the following ways. First, its major drawback is that it is relatively more difficult to reduce the size of the related endoscopic probe than the size of the mechanical scanning mechanism because it employs multiple transducer elements to detect ultrasound waves. Thus, problems, such as crosstalk or signal interference between channels, may occur and the cost of implementing the system may also be high. However, the electronic scanning mechanism has the following unique advantage over the mechanical scanning mechanism. That is, as the word "array" says, all of the one-dimensional signals (i.e., A-lines) required to produce a 2D or 3D tomographic image can be simultaneously obtained through the plurality of detection channels formed in an array transducer by only using a single shot of a laser pulse. This means that, without making any change to the sensor or probe position, a tomographic image covering a desired range of the target object may be acquired at one time, after just one laser pulse firing process. Consequently, in the current EUS technology utilized in clinics, the electronic scanning mechanism is mostly applied to EUS probes that are manufactured for the diagnosis of digestive diseases, for which high-level probe miniaturization is unnecessary.

In addition to the rapid scanning capability of the electronic scanning mechanism, another important merit of an array transducer in endoscopy is that an image display style and a field of view may be arbitrarily chosen, depending on the application direction, by appropriately changing the arrangement pattern of the ultrasonic sensor elements (i.e., array pattern) and their expansion range. Thus, various types of array probes have been developed and utilized in the current EUS technology, and they are typically classified into a side-scanning linear array probe, a radial-scanning array probe (or radial array probe), and a forward-scanning array probe depending on the arrangement pattern or scanning direction (see Prior Document 1).

Due to the aforementioned advantages and disadvantages of each of the scanning mechanisms, various PAE systems that adopt either of these two scanning mechanisms have been suggested, to date. Among them, representative examples of prior technologies that have adopted the array transducer-based electronic scanning mechanism (as also pursued by the present disclosure) include those presented in Prior Document 9 ($4^{th}$ IEEE Conference on Sensors 1&2, 704(2005)), Prior Document 10 (Optics Letters 35(13), 2266(2010)), Prior Document 11 (US Patent Application Publication No. 2011-0021924), Prior Document 12 (U.S. Pat. No. 8,932,223), Prior Document 13 (Proc. of SPIE 8943, 89432S(2014)), Prior Document 14 (Korean Patent Application Publication No. 2014-0126554), and Prior Document 15 (Proc. of SPIE 9708, 97080A(2016)).

Therefore, all the endoscopic systems disclosed in the prior documents have adopted a common system composition in which an array transducer is employed as the core part of acoustic signal detection, like conventional array transducer-based EUS probes, and then an optical fiber or illumination unit is placed around the array transducer to deliver laser light to the target tissue for PAI (note that the addition of the optical fiber is the major difference between a PAE probe and an EUS probe). However, there are obvious differences in the pattern of the employed array transducer, the detailed configuration between the array transducer and the light illumination unit placed around the array transducer, and the level of system realization. Detailed features of the prior systems will now be briefly reviewed and discussed with reference to FIGS. 15A through 15D and FIGS. 16A through 16C.

First, Prior Document 9, whose system is illustrated in FIG. 15A, might be the first document that proposes the concept that applies an ultrasonic "array transducer" to PAE. Moreover, this document disclosed a new type of an ultrasonic array sensor that can be fabricated like the typical mass production process of a semiconductor integrated circuit. However, Prior Document 9 only mentioned the possibility of applying this array sensor to PAE or intravascular imaging; it does not disclose any detailed shape or structure of a PAE probe or the associated implementation methods. Thus, the information presented in Prior Document 9 only focused on demonstrating the operation capability of the ultrasonic array sensor by performing a couple of phantom experiments.

However, in Prior Documents 10 through 15, more detailed system concepts or real embodiment results for a PAE application were disclosed in which related endoscopic probes started to have a more endoscope-like appearance; to some extent, these documents also addressed probe miniaturizations, which have the following features.

First, the endoscopic system disclosed in Prior Document 10, whose system is illustrated in FIG. 15B, has a structure that detects photoacoustic signals by using a ring type array transducer comprised of 64 elements, which are symmetrically placed around the central axis of the endoscope, and the light energy required for photoacoustic signal generation is delivered via a cone shape reflection mirror, which also is placed at the central axis of the endoscope next to the array transducer. However, the endoscopic system as is may not be applicable to a clinical endoscopic procedure because its probe is still too big (9 cm in length and 3 cm in diameter), and the glass material utilized for the probe encapsulation is not suitable for actual clinical use in terms of safety. Although its size could be reduced further, any detailed method or probe structure for how to reduce the probe size is not disclosed in Prior Document 10. Moreover, the endoscopic system of Prior Document 10 has a drawback in that a light emitting area (LEA) and an ultrasonic sensor area (USA) are spaced apart from each other (the problem caused by such an arrangement will be explained later).

Prior Documents 11 and 12, whose systems are illustrated in FIGS. 15C and 15D, present a couple of probe structures that can realize an intravascular PAE device by using an existing IVUS catheter probe. For example, Prior Document 11 presents information on a PAE probe constructed by employing an existing array transducer-based IVUS catheter probe as the basic frame of the probe, and multiple optical fibers are then placed at predetermined intervals around the surface of the catheter to enable photoacoustic imaging. However, the proposed structure has a disadvantage in that, since a limited number of optical fibers are simply added to the outer surface of an existing array transducer-based IVUS catheter, the intensity of light illumination may not be uniform over the 360° scan area, and the probe's flexibility may not be good enough. The non-uniformity issue of light illumination could be solved by placing optical fibers with a narrower diameter more densely. However, in this case, the probe flexibility may be seriously decreased in proportion to the total number of optical fibers that are used.

Prior Document 13, whose system is illustrated in FIG. 16A, presents another type of PAE probe with an actual embodiment result like the case shown in Prior Document 10. The major part of this work appears to be in the probe miniaturization result that achieved a diameter of 13.9 mm and a length of 60 mm, which are much smaller than those in the case discussed in Prior Document 10. However, the endoscopic probe presented in Prior Document 13 has a disadvantage in that, since the probe has a structure that obtains a photoacoustic signal by using only an 8-element-based array transducer, which is placed facing the distal end of the probe, a parabolic mirror, which has a 45°-tilted reflection surface and faces that array transducer, has to mechanically rotate in order to obtain a photoacoustic image over a desired scan range. Thus, the suggested scanning mechanism may not be a desirable direction for actual clinical use because the main purpose of using this type of array transducer is to avoid any mechanically moving component inside an endoscopic probe.

The endoscopic system disclosed in Prior Document 14 (FIG. 16B) also has a similar feature that adopts the combined electronic and mechanical scanning mechanism of an ultrasonic array transducer and a scanning mirror, like the case shown in Prior Document 13. Therefore, its image scanning process is fully accomplished by the additional mechanical scanning process provided by the scanning mirror. However, as mentioned above (Prior Document 13), the core benefit of employing an array transducer was not fully utilized, and the mismatch issue between an LEA and a USA still exists in this endoscopic system.

The endoscopic systems disclosed in Prior Document 15 (FIG. 16C) relate to a rigid probe developed for the diagnosis of prostate diseases via an anus insertion, i.e., transrectal imaging of the prostate. In an embodiment, a 192-element-based array transducer and a couple of optical fibers distributed around the array transducer are commonly placed facing the same direction on the same side of the probe to perform side-scanning. The main difference between this endoscopic probe and the previous endoscopic systems is that the employed array transducer is a linear type array transducer. In Prior Document 15, in addition to presenting the explained actual probe embodiment result, another probe design with a different configuration of optical illumination unit was also presented. However, in any case, the endoscopic structures presented in Prior Document 15 have the limitation that the LEA of an endoscopic probe is limited to the surrounding area of an array transducer or several spots that are discontinuously distributed around a linear array transducer. That is, the endoscopic probes also have a similar structure in that an LEA and a USA are completely separate from each other. This limitation was probably caused because the authors of Prior Document 15 only focused on a PAE probe embodiment by using an existing commercial ultrasonic array transducer, rather than focusing on working out an ideal probe structure that enables a uniform light illumination to an object to be examined over the entire area where the transducer elements are distributed. For reference, although not described in detail, an end portion of the probe that is actually implemented appears to be quite long, and it is described that its diameter is about 25 mm.

Until now, several key features of representative prior inventions that use an array transducer as a component for detecting a photoacoustic signal have been described. Although some other documents have also suggested PAE probes that have been developed based on a similar array transducer-based signal detection mechanism, those inventions did not describe the detailed shapes and structures of the endoscopes; thus, a detailed explanation was not given (for reference, Prior Document 8, which was published in 1997, was the first to suggest the endoscopic application of PAT by combining an ultrasonic detector and an optical illumination unit).

All the PAE probes disclosed in Prior Documents 10 through 15 can be classified as array transducer-based side-scanning endoscopic probes; among them, only the endoscopic probes shown in Prior Document 10 and Prior Document 11 adopted an array transducer-based radial-scanning mechanism as pursued by the present disclosure; however, the main application target of that probe is different from the current disclosure. Setting aside the additional future tasks that are required to achieve further miniaturizations of those endoscopic probes, which is actually the first thing that should be solved for a successful clinical translation, all of the endoscopic systems disclosed in Prior Documents 10 through 15 have the following fundamental drawbacks.

When any of the previous light illumination methods is utilized for a PAE probe, one biggest problem is that an optical illumination area (IA) formed inside an object and an ultrasonic scan area (SA) formed inside the object by the collective effect of the sensor elements that constitute an array transducer do not perfectly coincide. This occurs because, in most of the above-described prior inventions, light illumination units are simply added at some specific positions around an existing or typical style array transducer, which was actually manufactured for a conventional ultrasound imaging probe rather than for a PAE probe; resultantly, an LEA and a USA are formed separately. This leads to the following problem: light energy is not uniformly delivered over the entire scan area (i.e., SA) of an array transducer during its scanning process, so a dead zone occurs in an acquired photoacoustic image. For example, in the endoscopes disclosed in Prior Documents 10-12, a laser beam coincides with an ultrasonic scan plane formed by an array transducer only at a specific position (or radial distance) from the probe.

If any of the illumination methods suggested by the above inventions is utilized for a PAE probe, the discrepancy between an LEA and a USA may increase as the size of an array transducer (or a scan head) increases. Thus, in order to avoid this problem, one possible option would be to reduce the entire size of the scan head. However, if the size of a scanning head is reduced while maintaining any of the mentioned arrangement structures, one serious effect is that the maximum imaging depth of the PAE probe may be greatly reduced because the total available space for the scan head still has to be divided into the two compartments, i.e., an LEA and a USA, as the arrangement structure is preassumed. Here, the imaging depth decrease effect is also closely related to the maximally allowable light dose issue in accordance with the laser safety regulation described in the next section. It is true that, in prior inventions, an LEA is limited only to specific positions so the total amount of light energy that is actually delivered to an object to be examined may be significantly limited.

In general, the main purpose for using such an array transducer is to maximize the imaging performance in terms of imaging depth and imaging speed, rather than to facilitate probe miniaturization. Therefore, reducing the size of the probe may not be a desirable way to solve the aforementioned discrepancy issue.

Taken together, an array transducer-based PAE probe may be understood as a photoacoustic version of an array transducer-based EUS probe, which is currently utilized in clinics. This is a plausible comparison because, even in the PAE probe, although an optical illumination unit capable of transferring light energy to an object to be examined needs to be added, an ultrasonic array transducer is still a key element, just as it is in a conventional EUS probe.

In this regard, it is true that the above-described prior inventions, as well as any other similar apparatus that appropriately combines these two key elements, may have the potential to be used as a PAE probe if a certain level of probe miniaturization is achieved. However, in order to realize a useful endoscopic system that could be utilized in actual clinics, it is necessary to derive an advanced and more effective structure of a light illumination unit and an ultrasonic detection unit that can maximize the imaging performance within a restricted probe size, which is actually the point that the present disclosure aims to address.

PRIOR DOCUMENTS

Patent Documents

Prior Document 3: U.S. Pat. No. 4,543,960 (1985 Oct. 1)
Prior Document 4: U.S. Pat. No. 4,982,724 (1991 Jan. 8)
Prior Document 5: U.S. Pat. No. 5,125,411 (1992 Jun. 30)
Prior Document 6: U.S. Pat. No. 8,758,251 (2014 Jun. 24)
Prior Document 11: US Patent Application Publication No. 2011-0021924 (2011 Jan. 27)
Prior Document 12: U.S. Pat. No. 8,932,223 (2015 Jan. 13)
Prior Document 14: Korean Patent Application Publication No. 2014-0126554 (2014 Oct. 31)

Non-Patent Documents

Prior Document 1: Dietrich, C. Endoscopic Ultrasound: An Introductory Manual and Atlas, (Thieme, N.Y., 2006)
Prior Document 2: P. Hanrath et al., Chapter 31: "Transesophageal Horizontal and Sagittal Imaging of the Heart with a Phased Array System, Initial Clinical Results," in the book "Cardiovascular Diagnosis by Ultrasound," pp 280-288 (1982)
Prior Document 7: J M Yang, et al., "Photoacoustic endoscopy," Optics Letters 34(10), 1591 (2009)
Prior Document 8: Oraevsky, et al., "Laser optoacoustic tomography of layered tissues: signal processing," Proc. SPIE, 2979, 59 (1997)
Prior Document 9: 10 Wygant, et al., "Integrated ultrasound imaging systems based on capacitive micromachined ultrasonic transducer arrays," $4^{th}$ IEEE Conference on Sensors Vol. 1&2, 704 (2005)
Prior Document 10: Y Yuan, et al., "Preclinical photoacoustic imaging endoscope based on acousto-optic coaxial system using ring transducer array," Optics Letters 35(13), 2266 (2010)
Prior Document 13: D Tsyboulski, et al., "Dual modality optoacoustic and laser ultrasound endoscopy system," Proc. of SPIE 8943, 89432S (2014)
Prior Document 15: KL Bell, et al., "Integrated transrectal probe for translational ultrasound-photoacoustic imaging," Proc. of SPIE 9708, 97080A (2016)
Prior Document 16: Laser Institute of America, *American National Standard for Safe Use of Lasers*, ANSI Z136.1-2007, American National Standards Institute, Inc., New York (2007)
Prior Document 17: J M Yang, et al., "Simultaneous functional photoacoustic and ultrasonic endoscopy of internal organs in vivo," Nature Medicine 18(8), 1297 (2012)

SUMMARY

As mentioned above, the present disclosure relates to an array-transducer-based side-scanning PAE probe and system, and a main objective of the present disclosure is to provide a more advanced endoscopic structure that does not suffer from the mismatch issue between an optical illumination area (IA) and an ultrasonic scan area (SA) that exists in the prior inventions. More specifically, the present disclosure aims to work out a novel PAE probe structure with an imaging performance that is significantly better than that of existing PAE probes, especially in terms of imaging depth, by using a radial-scan array transducer as a signal detector in order to utilize the PAE probe to diagnose digestive diseases or heart diseases via a GI tract introduction.

First, the reasons why the probe structures suggested in the prior inventions described above have fundamental limits for use in GI endoscopy and are unable to achieve a large-depth imaging will be explained from a general technical viewpoint along with several key requirements that must be considered when designing a clinical endoscope.

In order to design a clinical endoscope, a specific application direction of the endoscope or a specific target object to be imaged must be decided first. This is important because thereafter basic specifications, such as the shape and the size of the endoscope, can be determined depending on the set application direction. In other words, unlike other general PAI systems (i.e., a non-endoscopic system), it is very important to find an effective structure because the available space of an imaging probe is very limited, and the effective probe structure or the main focus of a probe design may also vary depending on the application direction.

In the general video endoscopes and EUS probes utilized for clinical GI endoscopy, the diameter of the hose portion inserted into the human body typically ranges from ~1 cm to ~1.3 cm in order for the hose portion to be inserted into a digestive tract, such as the esophagus or the large intestine, without much difficulty. However, in order to add a probe steering function to those hose portions, such as the probe angulation capability, it is necessary to install a related unit at a point that is as close as possible to the distal end of a hose. This means that better probe steering performance can be achieved as the total length of a scanning head section, which is typically inflexible and in which an array transducer is installed, decreases.

On the contrary, if the scanning head section is formed too short, the space where an array transducer is to be installed is also reduced; consequently, the spatial angle (or the solid angle) for detecting the photoacoustic waves propagating from a signal source also decreases. This is similar to the well-known principle, known as the "limited-view problem", which is frequently discussed in conventional ultrasonography.

These two requirements conflict with each other; thus, an appropriate trade-off must be found when designing a probe. In the current array transducer-based EUS technology utilized for clinical GI endoscopy, for example, a related endoscopic probe is manufactured so that the length of the rigid scanning head section is equal to or less than ~3-4 cm, considering all these requirements.

Therefore, if a PAE probe is designed to be used like an existing array transducer-based EUS probe manufactured for GI tract imaging, both the array transducer and the illumination unit needed for PAI must be installed in the space allowed by the scanning head size, with a diameter of 1.3 cm or less and a length of approximately 3 cm (indeed, this is a requirement rather than an option).

If the discussed PAE probe must also provide large-depth imaging performance like existing array transducer-based EUS probes, the aforementioned size issue further complicates the situation. This is because, to achieve large-depth imaging, a sufficient amount of light energy must be delivered to an object to be examined, but the total area available for illumination—which can be calculated by subtracting the area required by the array transducer from the entire usable area (in this case ~8 cm$^2$, calculated from $\pi \times 1.3$ cm$\times 2$ cm and assuming a cylindrical shape) formed on the outer surface of the scanning head section—is significantly reduced.

In biomedical photoacoustics, it is well-known that the maximum imaging depth of a PAI system is mostly affected by the light illumination parameters rather than the sensitivity of an employed ultrasonic transducer. This is because the optical fluence distribution ($\Phi(r)$) of the photons inside a biological tissue (where the optical fluence [J/m$^2$] is defined as the energy flow of the photons per unit area regardless of the flow direction in a steady-state) shows a more sharp decay due to rapid optical diffusion, as shown in Formula 1, than the amplitude (A(z)) of the acoustic waves traveling in biological tissue (Formula 2).

$$\Phi(r) \propto \frac{e^{-\mu_{eff} r}}{r} \quad (1)$$

$$A(z, f) = A_0 e^{-a f^b z / 8.7} \quad (2)$$

For example, according to the two formulas, acoustic waves with a center frequency of 3 MHz have a penetration depth of about 2.9 cm, according to Formula 2, for soft tissue, such as muscle (here, 'a'-value for soft tissue was assumed as 1 dB cm$^{-1}$ MHz$^{-1}$ and b=1), whereas photons with a wavelength of about 720 nm and the highest optical penetration characteristics in biological tissue have a penetration depth of only 0.57 cm, according to Formula 1 (here $\mu_{eff}$=1.74 cm$^{-1}$ assumed). Here, the penetration depth was defined as the depth at which the exponential term at both falls to $e^{-1}$. However, it should be noted that, in Formula 1, the 1/r-term additionally exists, which makes the real penetration depth even lower.

Unlike conventional ultrasound imaging, in which an acoustic pulse is sent to the inside of a target object to be examined, first, and then a tomographic image of the object is produced by capturing the acoustic waves reflected from the object, PAI has to send a light pulse first; thus, as much light energy as possible has to be sent to the object in order to achieve large-depth imaging. Therefore, simply speaking, the imaging depth of a PAI system is mostly determined by how much energy can be delivered to the target object.

In this regard, it may be said that, in addition to the serious mismatch issue between an IA and an SA inside an object to be examined, existing array transducer-based PAE probes (Prior Documents 10 through 15) have such a light illumination structure that may not be able to achieve large-depth imaging. This is because the laser beams of those probes are emitted only through several specific points distributed around an array transducer; thus, the total amount of light energy that may be actually delivered to an object to be examined is very limited. When referring to the cases presented in Prior Documents 10 through 15, in which related PAE systems are physically implemented, the experimentally demonstrated imaging depth was limited to ~1 cm or less (in fact, the claimed imaging depth was not obtained from a real biological tissue; it came from an optical phantom). Indeed, the demonstrated imaging depth was much lower than the typical imaging depths of current array transducer-based EUS probes (Prior Documents 1) as well as those of the state-of-the-art PAI systems (typically known to be greater than 3 cm).

Of course, the above-described prior inventions may be able to further improve the imaging depth by simply increasing the amount of laser energy emitted through optical fibers (for example, as reported in Prior Document 11). However, in this case, those PAE systems may violate the safety limit regulations of the American National Standards Institute (ANSI) (see Prior Document 16), which state that the flow of light energy per unit area (1 cm$^2$) should not exceed 20 mJ, regardless of the flow direction anywhere on a surface of biological tissue during laser beam irradiation to the biological tissue.

In conclusion, most of the above-described inventions only focused on demonstrating the feasibility of a PAE system by using an array transducer; thus, their systems have fundamental limits in achieving an adequate probe size and large-depth imaging performance, which are required for GI endoscopy.

Therefore, the following essential conclusions are reached.

To maximize the imaging depth of a PAE probe within the typical probe size allowed in GI endoscopy, though a high-sensitivity ultrasonic transducer must be used, an illumination unit (i.e., an outlet) for the optical excitation of target tissue has to be carefully designed to emit the related laser beam as uniformly as possible over the widest possible region. In fact, this is the most important technical point to consider in designing such a PAE probe because, considering the safety limit (20 mJ/cm$^2$) and the maximum allowable size (1.3 cm in diameter and 2 cm in length) of the distal section, the total amount of laser energy that may be delivered to an object to be examined is limited to about 160 mJ—although one may use the entire distal section for the illumination purpose only.

Since the maximum imaging depth of a PAI system is a dependent variable that is determined, to some extent, by the illumination dose and the optical properties of the target tissue, a given probe space must be divided as effectively as possible for the illumination unit first, and other performance parameters (such as the sensitivity of the ultrasonic transducer) must also be optimized. For reference, the steady-state optical fluence distribution (Φ) formed inside a target object to be examined can be expressed approximately as a convolution of the spatial distribution $I(\vec{r}\,')$ of an incident beam onto the target surface and the Green's function $G(\vec{r}, \vec{r}\,')$, as shown in Formula 3, if the object is assumed as a semi-infinite homogenous medium (more exact formalism needs to reflect a boundary effect). And, it is known that the steady-state optical fluence distribution (i.e., Green's function) for a pencil beam incident to a target surface attenuates in a fashion similar to that seen in Formula 1. Thus, if the surface fluence does not exceed the safety limit, neither does the interior fluence.

$$\Phi(\vec{r}) = \int_S G(\vec{r}, \vec{r}\,') I(\vec{r}\,') ds' \qquad (3)$$

In summary, the key objective of the present disclosure is to provide a more advanced PAE probe structure that: 1) does not suffer from the mismatch issue between an IA and an SA that occurs in prior inventions and 2) enables large-depth imaging that approaches the theoretical limit of biomedical photoacoustics under the assumption of a typical probe size (~10-13 mm in diameter), allowed for clinical GI endoscopy, by using a radial array transducer as a signal detection mechanism and by adopting the general outer appearance and the typical size of conventional radial array transducer-based EUS probes as a morphological platform of the proposed PAE probe.

According to an aspect of the present disclosure, there is provided a photoacoustic and ultrasonic endoscope including an optical fiber; a light diffuser configured to radially diffuse a laser beam transmitted through the optical fiber; and an array transducer having a cylindrical shape and surrounding the light diffuser, the array transducer being configured to transmit the diffused laser beam therethrough and to generate an ultrasonic wave or detect an ultrasonic wave generated by an object to be examined.

The laser beam diffused by the light diffuser may pass through the entire area of a side surface of the array transducer.

A light emitting area from which the diffused laser beam exits the array transducer and an ultrasonic sensor area where the array transducer senses an ultrasonic wave may overlap each other.

The photoacoustic-ultrasonic endoscope according to an embodiment may further include an acoustic matching layer covering at least a portion of an outer surface of the array transducer and includes a light-transmissive material.

The acoustic matching layer may further include polymethylpentene (TPX).

The light diffuser may include a mirror located at a center of the array transducer and including a reflective surface capable of radially reflecting a laser beam transmitted through the optical fiber; and a beam shaper between the mirror and the optical fiber and configured to deflect the laser beam transmitted through the optical fiber such that a traveling direction of the laser beam is changed.

The beam shaper may include an electro-optic modulator (EOM) capable of focusing the laser beam in a particular direction.

The mirror may have a cone-like shape.

The mirror may have a pincushion-type shape.

The mirror may have a barrel-type shape.

The light diffuser may further include a cylindrical light scattering layer inside the array transducer and surrounding the mirror.

A reduced scattering coefficient ($\mu_s'$) of the light scattering layer may be equal to or greater than 0.1 cm$^{-1}$, and equal to or less than 1.0 cm$^{-1}$.

The light diffuser may include a prism located at a center of the array transducer and including a cone-like hole for radially diffusing a laser beam transmitted through the optical fiber; and a beam shaper between the prism and the optical fiber and configured to expand the laser beam transmitted through the optical fiber.

The array transducer may include a piezoelectric layer having a certain thickness; a plurality of first electrodes arranged on a first surface of the piezoelectric layer in the form of an one-dimensional or two-dimensional array; and a plurality of second electrodes on a second surface of the piezoelectric layer, the second surface being opposite the first surface, and the second electrodes being arranged parallel to the plurality of first electrodes.

The photoacoustic-ultrasonic endoscope may further include an optically-transparent backing layer between the light diffuser and the piezoelectric layer.

The first electrode and the second electrode may be optically-transparent electrodes.

The first electrodes and second electrodes may each independently include any one of a group consisting of indium tin oxide (ITO), indium zinc oxide (IZO), zinc oxide (ZnO), indium oxide (In$_2$O$_3$), Ge-doped In$_2$O$_3$ (IGO), and aluminum-doped zinc oxide (AZO).

The plurality of first electrodes and the plurality of second electrodes may include opaque electrodes.

The photoacoustic-ultrasonic endoscope may further include a light reflecting layer between the second electrode and the light diffuser.

The array transducer may include a first array transducer layer including a ceramic or single crystal-based piezoelectric material; and a second array transducer layer surrounding the first array transducer layer and including a polymer-based piezoelectric material.

According to another aspect of the present disclosure, there is provided a photoacoustic and ultrasonic endoscope including an optical fiber; an insertion hose surrounding and protecting the optical fiber; a hose end frame provided at one end of the insertion hose; and a scanning head provided at one end of the hose end frame and detachably attached to the hose end frame, wherein the scanning head includes a light diffuser configured to radially diffuse a laser beam transmitted through the optical fiber; and an array transducer having a cylindrical shape and surrounding the light diffuser, the array transducer being configured to transmit the diffused laser beam therethrough and to generate an ultrasonic wave or detect an ultrasonic wave generated by an object to be examined.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings in which:

FIGS. 15A through 15D and 16A through 16C are views illustrating the endoscopic structures of Prior Documents 9 through 15.

DETAILED DESCRIPTION

Figure 1:
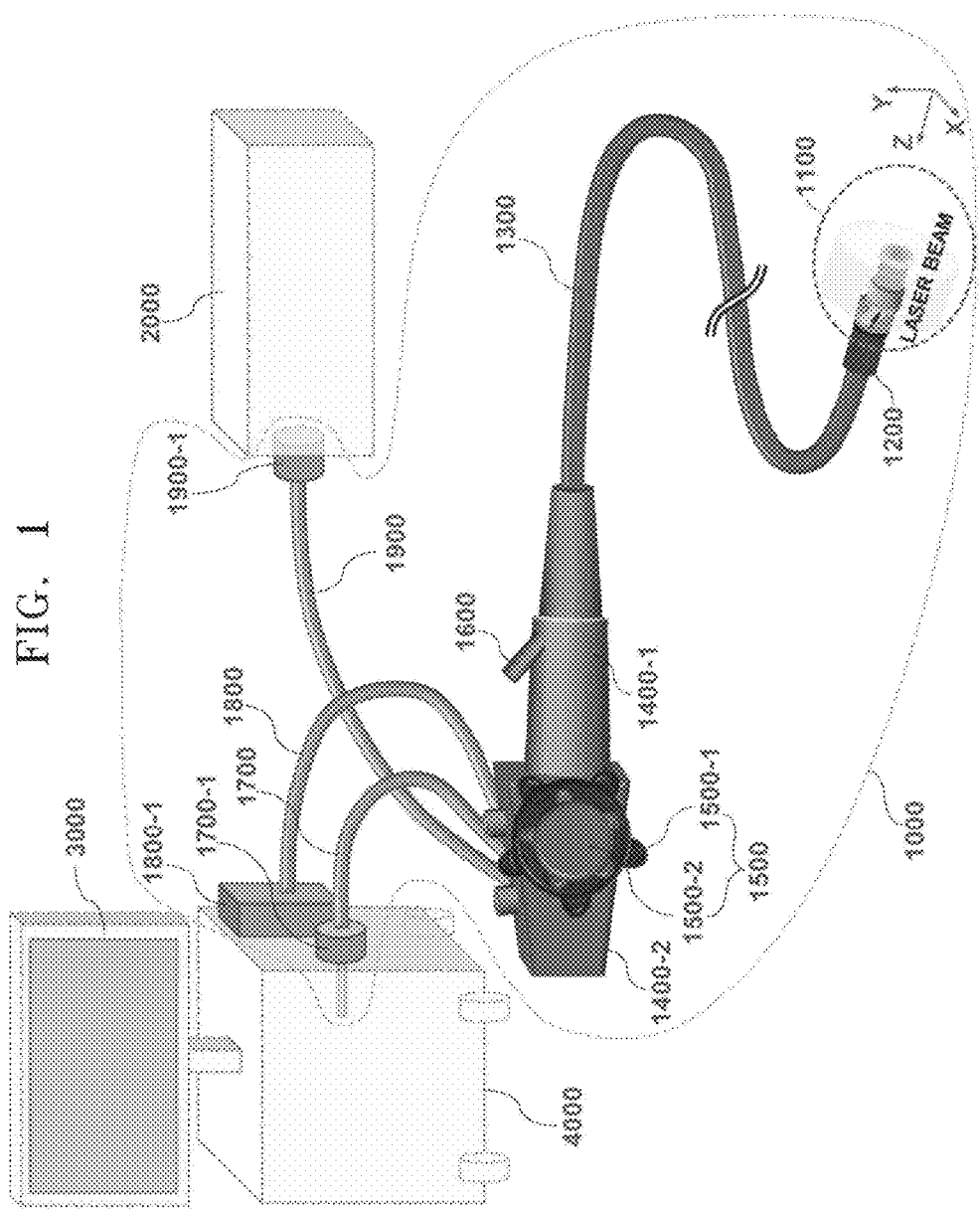
FIG. 1 is a view illustrating an overall composition and configuration of a radial array transducer-based photoacoustic-ultrasonic endoscopic system according to an embodiment.

The present disclosure may include various embodiments and modifications, and embodiments thereof will be illustrated in the drawings and will be described herein in detail. The advantages and features of the present disclosure and methods of achieving the advantages and features will be described more fully with reference to the accompanying drawings, in which embodiments are shown. The present disclosure may, however, be embodied in many different forms and should not be construed as being limited to the embodiments set forth herein.

Reference will now be made in detail to embodiments, examples of which are illustrated in the accompanying drawings. In the drawings, the same elements are denoted by the same reference numerals, and a repeated explanation thereof will not be given.

It will be understood that although the terms "first", "second", etc. may be used herein to describe various elements, these elements should not be limited by these terms. These elements are only used to distinguish one element from another.

As used herein, the singular forms "a", "an", and "the" are intended to include the plural forms as well, unless the context clearly indicates otherwise.

It will be further understood that the terms "comprises" and/or "comprising" used herein specify the presence of stated features or components, but do not preclude the presence or addition of one or more other features or components.

It will be understood that when an element is referred to as being "connected to" another element, it may be directly or indirectly connected to the other element. That is, for example, intervening elements may be present.

Expressions such as "at least one of", when preceding a list of elements, modify the entire list of elements and do not modify the individual elements of the list.

FIG. 1 is a view illustrating an overall composition and configuration of a radial array transducer-based photoacoustic-ultrasonic (i.e., dual-mode) endoscopic system (hereinafter, also referred to as a PAE-EUS system) according to an embodiment. FIG. 1 illustrates a photoacoustic-ultrasonic endoscopic probe (hereinafter, the imaging probe is referred to as a PAE-EUS probe), peripheral systems for operating the PAE-EUS probe, and a connection relationship between the PAE-EUS probe and the peripheral systems.

Referring to FIG. 1, a PAE-EUS system according to an embodiment may include a PAE-EUS probe 1000 including a distal section 1100, an angulation section 1200, an insertion hose 1300, base grips 1400-1 and 1400-2, a direction control knob 1500, an accessory channel inlet 1600, a probe-console communication cable 1700, a transducer data cable 1800, and a guiding optical fiber cable 1900; a laser source 2000 that provides pulse-type light energy needed for photoacoustic imaging to the PAE-EUS probe 1000; and a system console 4000 that controls the PAE-EUS probe 1000, receives a detected photoacoustic signal and an ultrasonic signal from the PAE-EUS probe 1000, appropriately processes the photoacoustic signal and the ultrasonic signal, and displays the processed photoacoustic image and the ultrasonic image on a monitor 3000.

As described above, one of the objectives of the present disclosure is to provide a new configuration of the distal section 1100 that may solve the many limitations of existing array transducer-based PAE systems, e.g., insufficient probe miniaturization and poor imaging depth, by adopting the general shape and size of existing radial array transducer-based EUS probes (i.e., radial scanning EUS probes) utilized for GI endoscopy as a basic platform of the proposed device design.

Accordingly, due to this motivation, the general outer appearance of the PAE-EUS probe 1000 is similar to that of an existing array transducer-based EUS probe. However, the internal structure of the distal section 1100 is completely different from that of the existing array transducer-based EUS probe, and many elements, such as the guiding optical fiber cable 1900, which delivers a laser beam from the laser source 2000 to the PAE-EUS probe 1000, are added to the PAE-EUS probe 1000 to enable PAI. The function of each element will now be briefly explained with reference to FIG. 1.

The distal section 1100 is a key portion in which a light illumination unit and an ultrasonic detection unit are installed, and the distal section 1100 is inserted into an object to be examined during an actual endoscopic procedure to acquire a photoacoustic image or an ultrasonic image. First, the distal section 1100 may be implemented to have a diameter ranging from, but not limited to, about 1 cm to about 1.3 cm, in order to be applied to a GI endoscopy, as pursued by the present disclosure. The angulation section 1200 has a probe steering function, such as angulation or bending, so that the direction of the distal section 1100 can be effectively steered when the distal section 1100 approaches a target point along a narrow and curved path. That is, the angulation section 1200 can be bent along the X-Z plane that is perpendicular to the Y-axis that is coincident with the endoscopic hose axis, by manipulating the two direction control knobs 1500-1 and 1500-2 that are installed at the base of the PAE-EUS probe 1000. The insertion hose 1300, which is the main body of the PAE-EUS probe 1000, is physically flexible and has a slender and long hose-like shape; thus, it may allow the distal section 1100 to be effectively inserted into the target point, which might only be accessible through a narrow and curved path. The insertion hose 1300 may have a diameter ranging from about 1 cm to about 1.3 cm, which is similar to that of the distal section 1100, and a length ranging from about 0.8 m to about 2 m. The outer surface of the insertion hose 1300 may be coated with a thin layer of a soft and flexible polymer, as is the case with an existing clinical video endoscope. A number of electric wires and optical fibers pass through the inside of the insertion hose 1300, and additional channels may also be formed inside the insertion hose 1300. More details on the internal structure of the insertion hose 1300 will be described later.

The base grips 1400-1 and 1400-2 that allow a clinician to hold and manipulate the PAE-EUS probe 1000 easily may be formed near the base part of the insertion hose 1300, and the accessory channel inlet 1600, through which an accessory instrument may be inserted, protrudes obliquely from a side of the base grip 1400-1. The accessory channel inlet 1600 may have an internal diameter ranging from about 2.7 mm to about 3.8 mm in general, and thus a variety of accessory instruments may be introduced into the accessory channel inlet 1600. An inserted accessory instrument may pass through the insertion hose 1300 and be projected from an accessory channel outlet 1170 (see FIG. 2) installed at the distal section 1100.

Three different (or multiple) types of cables may be connected to one side of the base grips 1400-1 and 1400-2 (e.g., 1400-2, as shown in FIG. 1). One cable is the guiding optical fiber cable 1900 in which an optical fiber or optical fiber bundle for delivering a laser beam emitted from the laser source 2000 to the base grip 1400 is embedded. The guiding optical fiber cable 1900 may be connected to the laser source 2000 via a guiding optical fiber cable adapter 1900-1, and the opposite end of the guiding optical fiber cable 1900 may be connected to the optical fiber 1113 (see FIG. 2) that is located inside the insertion hose 1300 (see FIG. 2). Alternatively, the guiding optical fiber cable 1900 may be a part (i.e., a physical extension) of the optical fiber 1113. Another cable is the probe-console communication cable 1700 that includes a number of electric wires configured to control the overall operational process of the PAE-EUS probe 1000 and transmit a video image provided by a small charge-coupled device (CCD) camera 1150 mounted in the distal section 1100. The probe-console communication cable 1700 is connected to the system console 4000 via a probe-console communication cable adapter 1700-1. The last cable is the transducer data cable 1800 that transmits a photoacoustic signal and an ultrasonic signal detected by the array transducer 1111, which will be explained later. The transducer data cable 1800 may also transmit a series of electric pulses to the array transducer 1111 when an ultrasound imaging mode is initiated. The transducer data cable 1800 is also connected to the system console 4000 via a transducer data cable adapter 1800-1.

The configurations and functions of several major parts of the PAE-EUS probe 1000 and its peripheral systems have been briefly explained. For reference, the system composition and configuration shown in FIG. 1 is only an example provided for better understanding; some other subsidiary elements may be added and, if necessary, the laser source 2000 and the system console 4000 may be integrated as a single unit. In this case, the probe-console communication cable 1700, the transducer data cable 1800, and the guiding optical fiber cable 1900 have to be appropriately modified, and they may be integrated into a single cable.

As was previously mentioned, one of the main objectives of the present disclosure is to provide an advanced scanning head structure that leads to a better imaging depth than those of existing PAE systems while maintaining a conventional image scanning (or image presentation) style—such as a two-dimensional (2D) plane or a three-dimensional (3D) disc-like image—and the outward appearance and size of radial array transducer-based EUS probes currently used in clinics.

Figure 2:
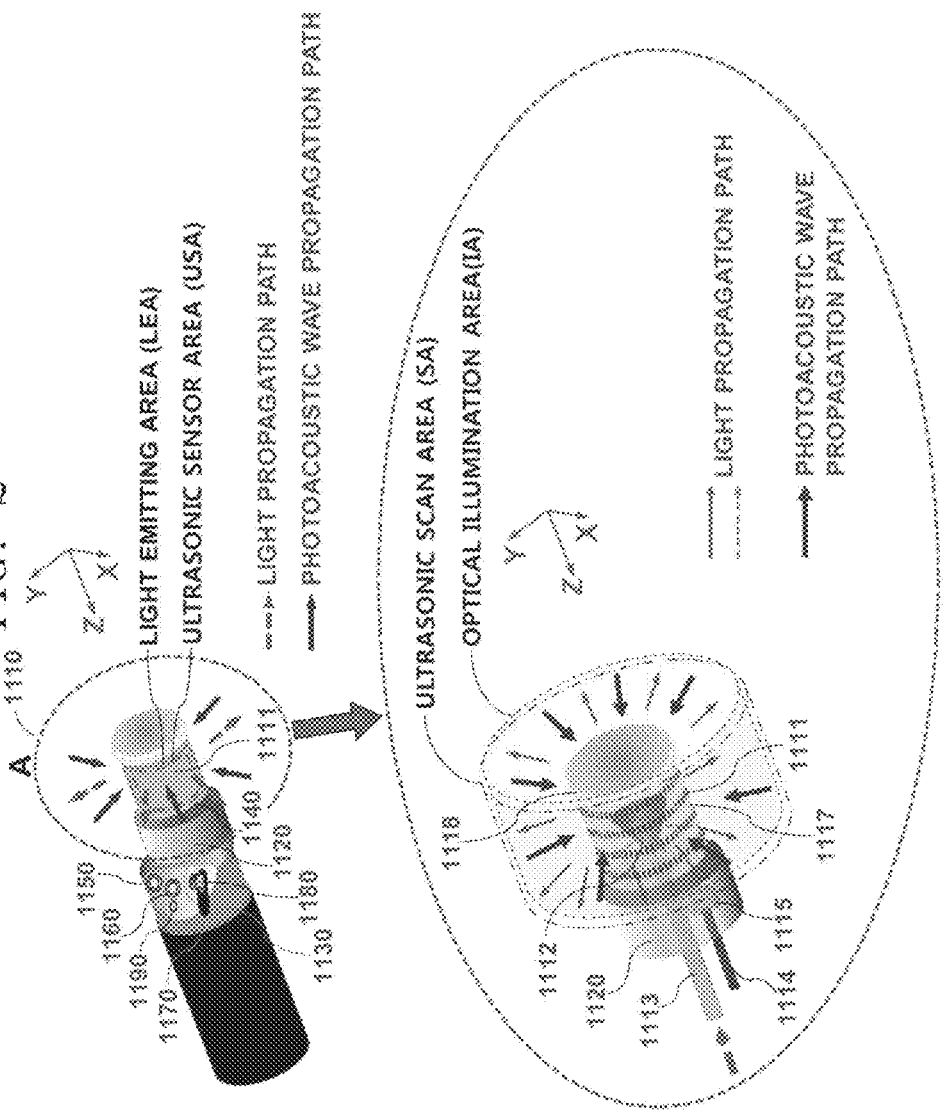
FIG. 2 is a schematic diagram illustrating the outer appearance of the distal section of a photoacoustic-ultrasonic endoscopic probe and a perspective view of the interior of a scanning head according to an embodiment.

FIG. 2 shows one of the embodiments derived to achieve this objective; it illustrates the structure of an embodiment of a distal section 1100, including a scanning head 1110 and other major elements distributed around the scanning head 1110, and a magnified 3D perspective view (i.e., the bottom image enclosed by a dashed circle) showing the interior of region A, which shows how the light illumination unit and the ultrasonic detection unit are configured inside the scanning head 1110.

Briefly speaking, in order to maximize the imaging depth according to the general principle of PAI within the available size of about 1.3 cm in diameter and 2 cm in length and the outer appearance of a scanning head, the present disclosure has worked out an internal structure of the scanning head 1110, which includes a light diffuser 1112 and an optically-transparent array transducer 1111 as core elements.

First, referring to FIG. 2, the main elements of the distal section 1100 and basic functions of the elements according to an embodiment will now be explained.

As mentioned, FIG. 2 illustrates the distal section 1100, which is an end portion of the entire PAE-EUS probe 1000 shown in FIG. 1; the distal section 1100 is connected to the angulation section 1200, and it includes the scanning head 1110. First, the scanning head 1110 is the key portion to which a core concept of the present disclosure is applied, and when a PAI mode is initiated, the scanning head 1110 approaches a target point to be examined, emits a laser beam, and detects a generated photoacoustic signal. The scanning head 1110 may be firmly fixed by the scanning head base frame 1120, which bridges the scanning head 1110 and the hose end frame 1130, and, on the distal end of the scanning head 1110, a first groove for balloon fixation 1118 may be formed. The first groove for balloon fixation 1118 may be a ring-shape groove, and it can be used for mounting an acoustic matching balloon, which might be needed for an actual endoscopic procedure, along with the second groove for balloon fixation 1140, which is formed between the scanning head 1110 and the scanning head base frame 1120. A detailed method for using the first/second groove for balloon fixation 1118/1140 will be explained later.

A small CCD camera 1150 may be installed on an inclined side of the hose end frame 1130 in order to provide real-time video images; this enables the PAE-EUS probe 1000 to more effectively approach a target point to be examined during an actual clinical procedure. Moreover, a visual-field illumination unit 1160 that provides light with a predetermined color may be installed next to the small CCD camera 1150 so that the small CCD camera 1150 could clearly image objects even in a dark condition.

A hole, similar to a coin slot, may also be formed in the inclined side of the hose end frame 1130 so that the accessory channel outlet 1170 and a biopsy needle lever 1180 can be installed inside the hole. The biopsy needle lever 1180, which can be installed next to the accessory channel outlet 1170, could be utilized to adjust the direction of a biopsy needle (not shown) projected from the accessory channel outlet 1170 so that fine needle aspiration (FNA), or a similar procedure, could be effectively performed based on the combined photoacoustic-ultrasonic dual-mode image provided by the present endoscopic system. The mentioned biopsy needle (not shown) may be inserted into the accessory channel inlet 1600, shown in FIG. 1, advanced forward along a predetermined channel (i.e., the accessory channel) formed inside the insertion hose 1300, and then ejected from the predetermined channel via the accessory channel outlet 1170 shown in FIG. 2. For the manipulation of the biopsy needle lever 1180, an additional apparatus with a shape like a dial or a trigger may be installed near the base grips 1400-1, 1400-2.

In addition, a waterjet nozzle 1190, for washing out the unwanted materials attached to a surface of the small CCD camera 1150 or the like, at any time during the process of inserting the scanning head 1110 of the PAE-EUS probe 1000 into the object to be examined, may be installed on an edge of the inclined side of the hose end frame 1130.

While the main elements of the distal section 1100 have been explained, the elements shown in FIG. 2 are only several examples of possible embodiments that may be necessary to effectively realize the main concept derived from the present disclosure; thus, some other system elements, obviously required by common sense, may be added, elements that are not essentially required may be excluded, and the positions of the aforementioned elements may also be changed depending on application direction. For example, the hose end frame 1130 and the scanning head base frame 1120 may be formed as a single piece rather than separate pieces; the positions of the visual-field illumination unit 1160, the small CCD camera 1150, the accessory channel outlet 1170 and the biopsy needle lever 1180 may be rearranged; and the numbers of visual-field illumination units 1160 and small CCD cameras 1150 may also be increased. Additionally, the position of the second groove for balloon fixation 1140 can be shifted between the scanning head base frame 1120 and the hose end frame 1130.

Referring to FIG. 2, more details on the structure of the PAE-EUS probe 1000 that includes the light diffuser 1112 and the array transducer 1111, whose concepts have been worked out to maximize both the light emitting area and the span area of the array transducer 1111 within a restricted area (typically about 8 cm$^2$ when considering the total surface area of the scanning head 1110), will be explained.

According to the present disclosure, a PAE-EUS probe 1000 includes the optical fiber 1113; the light diffuser 1112 which is configured to radially diffuse the laser beam delivered through the optical fiber 1113 to a target point to be examined; and the ring-shaped array transducer 1111 through which the diffused laser beam may pass and also be configured to generate ultrasonic pulses or detect the ultrasonic or photoacoustic waves propagating from the target point in a form that it surrounds the light diffuser 1112.

According to an embodiment, the laser beam emitted from the light diffuser 1112 is able to pass through the side of the scanning head 1110 with a cylindrical shape (i.e., where the array transducer 1111 is distributed). In other words, the laser beam may pass through the entire span area of the transducer elements comprising the ring-shaped array transducer 1111.

According to an embodiment, the light emitting area (LEA), through which the diffused laser beam is emitted from a scanning head 1110, and the ultrasonic sensor area (USA), where multiple ultrasonic sensor elements are distributed constituting an array transducer 1111, overlap each other.

Referring to FIG. 2, the laser beam is emitted from the scanning head 1110 by passing through the array transducer 1111 and sent to an object (not shown) to be examined.

In general, the light emitting area (LEA) of an imaging device refers to the area through which illumination light is emitted. However, as it was previously stated that the LEA according to the present disclosure overlaps with the USA where the array transducer 1111 is distributed, the inner or outer surface of the array transducer 1111 becomes both the LEA and the USA.

Due to the unique structure, the aforementioned mismatch issue between an optical IA and an ultrasonic SA and the limited illumination energy problems of the prior inventions can be solved simultaneously.

Referring to the perspective view presented in FIG. 2 (i.e., the lower image) in which the internal structure of the scanning head 1110 is shown, one or more strands of optical fiber 1113 are placed inside the insertion hose 1300 and extend to the distal section 1100 of the PAE-EUS probe 1000. Thus, a laser beam delivered through the optical fiber 1113 is diffused and expanded over the entire area where the array transducer 1111 is distributed by the light diffuser 1112, which is located at the central region of the array transducer 1111, passes through the array transducer 1111, and is then sent to a target object.

For reference, the light diffuser 1112 shown in FIG. 2 represents only a concept rather than depicting its shape or structure. However, it must somehow play a role in changing the direction of, and expanding, the laser beam emitted from the optical fiber 1113 to the whole ring-shaped array transducer 1111 area. Thus, the construction of the light diffuser 1112 may utilize such optical elements as lenses, mirrors, and diffusers with a specific shape; but it will not be limited to these items, and a complex module composed of articles beyond the mentioned optical elements may be designed.

The PAE-EUS probe according to an embodiment may further include an acoustic matching layer 1117 that covers at least a portion of the outer surface of the array transducer 1111 and made of a material through which light can be transmitted.

Referring to the perspective view presented in FIG. 2 (i.e., the lower image), a surface of the array transducer 1111 may be covered with the acoustic matching layer 1117 made of a polymer-based material in order to protect the surface of the array transducer 1111 and provide an adequate acoustic matching condition between the array transducer 1111 and an object or ambient immersion medium. Consequently, the acoustic matching layer 1117 also needs to be optically-transparent; it may be preferable that the acoustic matching layer 1117 be made of a polymethylpentene (TPX)-based material due to the required acoustic and optical characteristics. For reference, TPX is a material that permits light to be very easily transmitted therethrough, and it also has low acoustic impedance close to that of the general soft tissues of humans.

Once the laser beam that consecutively passes through the array transducer 1111 and the acoustic matching layer 1117 penetrates the surface of an object, it is rapidly diffused and absorbed, thereby generating photoacoustic waves. Afterwards, some of these photoacoustic waves propagate to the array transducer 1111, where they are detected and finally converted into an electrical signal according to the piezoelectric effect of the array transducer 1111. Thus, the array transducer 1111 described by the present disclosure is such a component that can detect photoacoustic waves based on the piezoelectric effect and also can send ultrasonic pulses to an object and detect reflected waves when the ultrasonic imaging mode is initiated, as in conventional PAI systems.

For reference, when a laser beam penetrates a target object, an approximate intensity distribution of photons inside the target tissue can be calculated based on Formula 1 and Formula 3, but the main feature that differentiates the described endoscope from prior PAE systems is that the light energy required for the photoacoustic excitation of target tissue can be more effectively spread over the entire SA of the array transducer 1111, which eventually induces more uniformly-distributed photoacoustic waves. That is, by overlapping the LEA and the USA, it is possible to achieve an overlapping effect of the IA and the SA.

After the photoacoustic waves are converted into electrical signals by the multiple piezoelectric elements constituting the array transducer 1111, the signals are sent to a cable splitter 1115 via the multiple electric wires (not shown) connected to each transducer element; the signals are then delivered to the system console 4000 and further pass through the electric wire bundle 1114 installed inside the insertion hose 1300 of the PAE-EUS probe 1000. Due to the explained principle, the electric wire bundle 1114 originating at the scanning head 1110 may extend to the transducer data cable adapter 1800-1, shown in FIG. 1, as a continuous unit connected to the transducer data cable 1800. Here, the cable splitter 1115 may function simply as a junction or connection point that electrically connects the multiple electric wires connected to each transducer element (not shown) inside the scanning head 1110 to the electric wire bundle 1114 in the insertion hose 1300. However, if necessary, the cable splitter 1115 may also offer other functions, such as pre-amplification and multiplexing.

Since the PAE-EUS system, according to the present disclosure, includes the array transducer 1111 as an ultrasound detector, the PAE-EUS system can provide not only a photoacoustic image but also a conventional ultrasound image. Thus, if an ultrasound imaging mode is initiated, a series of electrical pulses, which are set to have specific phases that are different from one another according to a predetermined purpose, are generated from the system console 4000 and sent to the individual piezoelectric elements of the array transducer 1111 to generate ultrasonic pulses, after sequentially passing through the transducer data cable 1800 and the insertion hose 1300. Then, the generated ultrasound pulses propagate toward the object, and a portion of the ultrasound pulses are bounced back from the object and detected by the array transducer 1111; they are then further delivered to the system console 4000 in reverse order of the explained pulsing process, and finally displayed as an image on the monitor 3000.

Such photoacoustic-ultrasonic dual-mode imaging sequences may occur very quickly and alternately at a predetermined time interval, as described in Prior Document 17, and pieces of the data obtained according to the photoacoustic-ultrasonic imaging sequence may be processed once a predetermined amount of data set is obtained, and this may be simultaneously displayed on the monitor 3000.

In conclusion, the array transducer 1111, according to the present disclosure, must have the capability of transmitting a laser beam very effectively therethrough as well as the conventional ultrasound pulsing and detecting function. Several possible embodiments will be presented later.

Figure 3A:
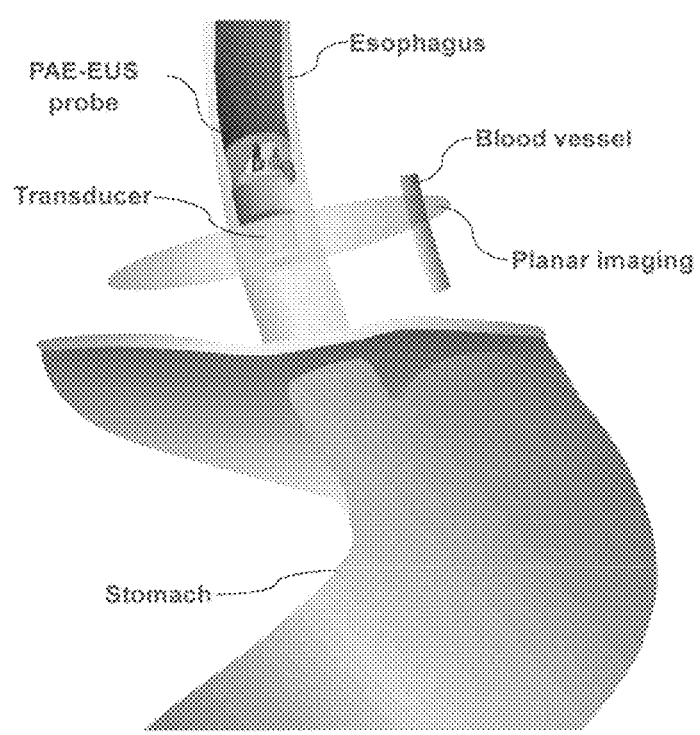
FIGS. 3A and 3B are schematic diagrams illustrating the 2D or 3D scanning mechanism of a photoacoustic-ultrasonic endoscopic probe according to an embodiment.
Figure 3B:
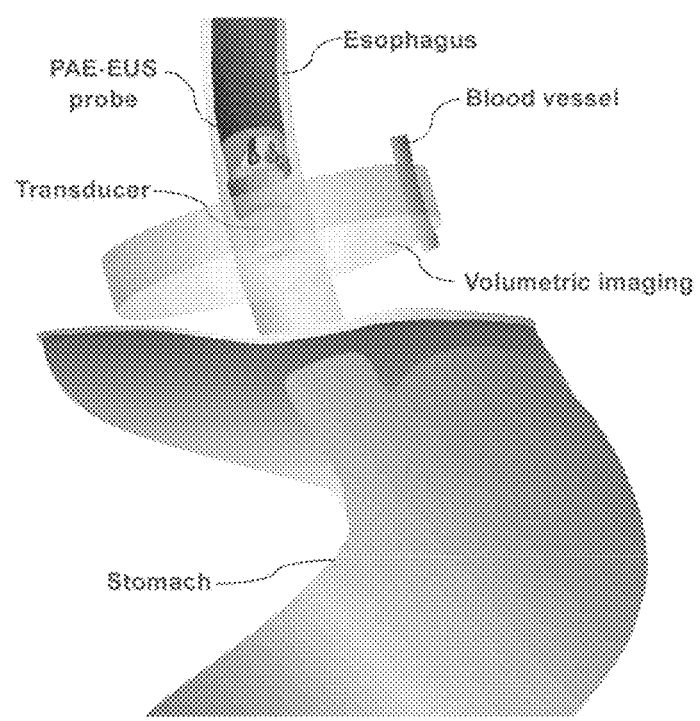

FIGS. 3A and 3B are schematic diagrams that illustrates the 2D and 3D scanning mechanism of a PAE-EUS probe according to an embodiment.

Referring to FIGS. 3A and 3B, either two-dimensional circular (FIG. 3A) or three-dimensional volumetric (FIG. 3B) photoacoustic and ultrasonic images are obtainable by using one of the endoscopic embodiments provided by the present disclosure within the region of interest inside a specimen.

According to an embodiment of the present disclosure, it is possible to visualize major blood vessels and neighboring organs distributed around the GI tract over a 360° full angular field of view because the light diffuser 1112 disperse the laser beam radially in all directions. Of course, in addition to the structural image information provided by the endoscopic system, it is also possible to provide functional information such as the oxygen saturation of hemoglobin ($sO_2$) by using different types of laser beams with two or more wavelengths, as demonstrated in Prior Document 17.

Unlike prior inventions (in particular Prior Document 10), one of the main concepts of the present disclosure to achieve a large-depth imaging performance is to overlap the LEA and the USA by placing a light diffuser 1112 in the central region of the optically-transparent array transducer 1111. Hereinafter, referring to FIGS. 4 through 12, possible embodiments of a light diffuser 1112 and an array transducer 1111 are explained.

Figure 4:
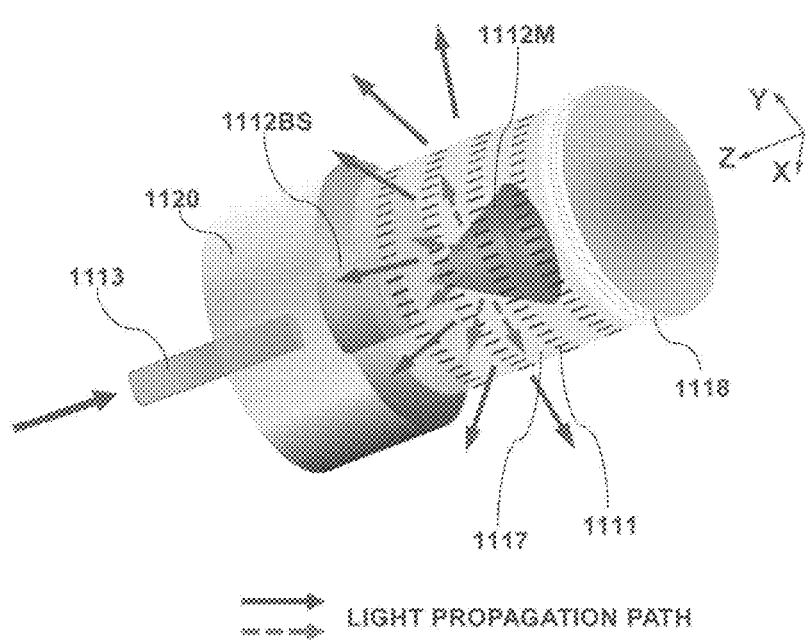
FIG. 4 is a perspective view showing the configuration of a light diffuser and corresponding light propagation path inside a scanning head according to an embodiment.

FIG. 4 is a perspective view showing the configuration of a light diffuser and corresponding light propagation path inside a scanning head according to an embodiment.

In general, in an array transducer-based PAE probe, an electric wire bundle that carries photoacoustic signals must pass through the probe's insertion hose as it does in a conventional EUS probe. This means that the final space allowed for optical fiber installation is limited. Hence, considering the general thickness of the insertion hose of a clinical EUS probe (i.e., ~10-13 mm in diameter), the maximum size allowable for optical fiber installation may only be about 5 mm in diameter including its jacket thickness. This eventually causes the optical fluence at the outlet of the optical fiber to be very high. Moreover, due to the numerical aperture (NA) of the optical fiber, the laser beam emitted through the optical fiber shows diverging behavior in proportion to the NA. That is to say, individual photons emitted from the optical fiber may propagate irregularly rather than being collimated.

Under both the explained system condition and other system requirements, for the laser beam emitted through the optical fiber 1113 to be spread uniformly over the entire 360° area where the array transducer 1111 is distributed, the scanning head 1110 of a PAE-EUS probe 1000 according to an embodiment may include an optical reflector with a predetermined reflection surface (or predetermined optical diffusion function) located at the central region of the array transducer 1111.

According to an embodiment, a light diffuser 1112 may include a mirror 1112M which is positioned at the center of the array transducer 1111 and has a reflection surface that radially spreads the laser beam delivered from the optical fiber 1113 in all directions and also include a beam shaper 1112BS which is positioned between the mirror 1112M and the optical fiber 1113 and expands or performs a changing function for the propagation direction of the laser beam delivered from the optical fiber 1113.

Referring to FIG. 4, a beam shaper 1112BS is placed between the end of an optical fiber 1113 and a mirror 1112M to expand the laser beam emitted from the optical fiber 1113 and also deflect the propagation of the expanded laser beam toward a predetermined direction. That is, an optical fiber 1113, a beam shaper 1112BS, and a mirror 1112M may be placed co-axially along the central axis of the scanning head 1110 (i.e., Z-axis) and in the mentioned order.

In this instance, to effectively reflect the laser beam, at least a portion of the outer surface of the mirror 1112M may be coated with a light reflection layer, and through the mentioned arrangement and feature, the laser beam emitted from the optical fiber 1113 may be evenly dispersed over the entire area where the array transducer 1111 spans.

FIGS. 5A through 5D are views showing the optical compositions and corresponding light propagation paths inside a scanning head 1110 according to various embodiments.

The beam shaper 1112BS according to an embodiment may include an electro-optic modulator (EOM) 1112BS-EOM that has the ability to send or deflect the laser beam reflecting off the mirror 1112M to specific 8-directions with respect to the Z-axis.

Figure 5A:
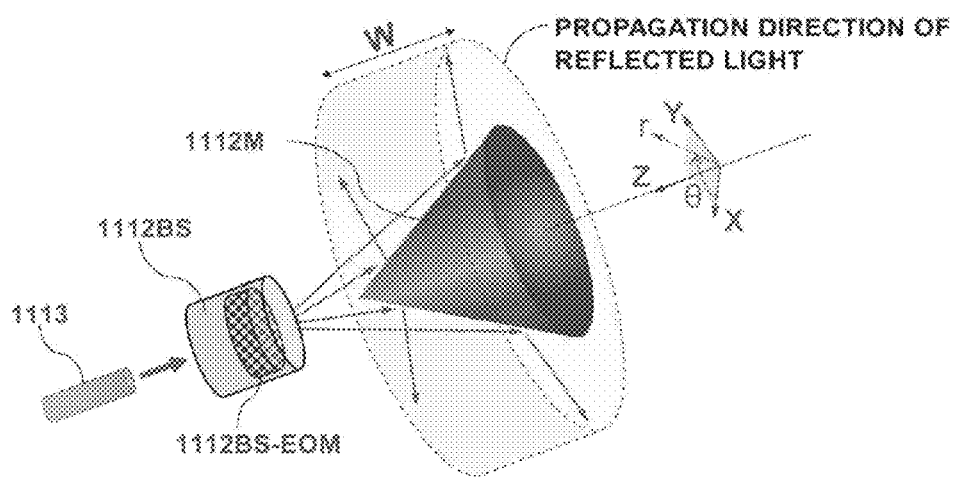
FIGS. 5A through 5D are views showing the optical compositions and corresponding light propagation paths inside a scanning head according to various embodiments.

Referring to FIG. 5A, if the beam shaper 1112BS includes an EOM, it is possible for the laser beam to reflect off of the mirror (1112M) and be evenly emitted over a 360° radial plane, while also focusing on a time-specific 8-direction.

In order to send more laser energy to a particular direction or to focus onto a small spot, the EOM allows for the modulation or steering of the laser beam in space and time.

Thus, the concept of EOM encompasses all possible elements with a much more diverse form and function than the common "EOM" device used in the optics field, including the digital micromirror device (DMD), the liquid crystal-based spatial light modulator (SLM), and the general EOM device operated through the typical piezoelectric principle.

According to an embodiment, the mirror 1112M could be structured into a cone. If a cone shaped mirror 1112M is used, the laser beams leaving the array transducer 1111 can be distributed in a spatially-uniform way across a 360° radial plane, as well as be quasi-parallel with respect to the transverse plane of the longitudinal Z-axis.

According to an embodiment, the mirror 1112M can be structured as either a horn-like cone (herein, a term "pincushion-type" is used to express the feature) or a beanie hat-like cone (herein, a term "barrel-type" is used to express the feature). In other words, the mirror 1112M may have curved (i.e., not straight), cone-shaped sides.

Figure 5B:
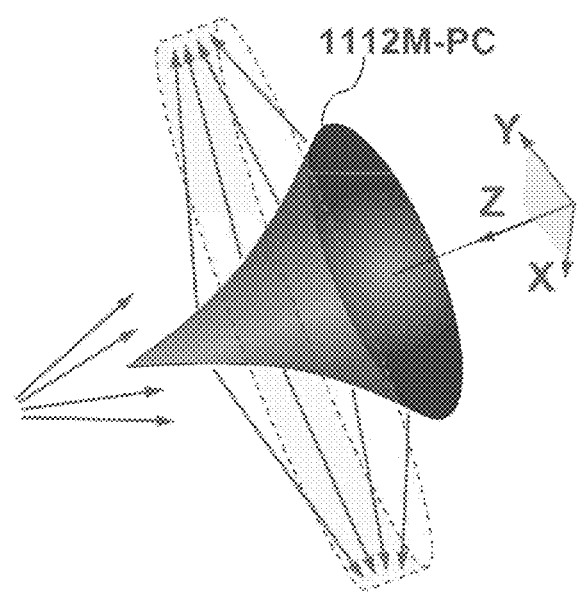
Figure 5C:
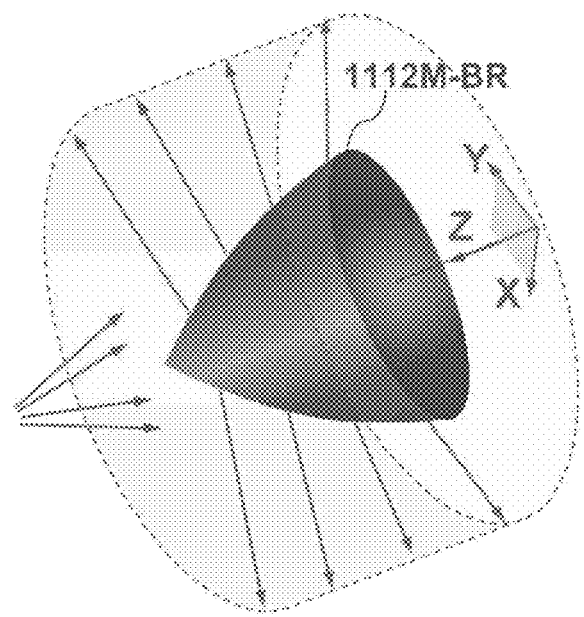

Referring to FIGS. 5B and 5C, the mirror 1112M may have either a pincushion-type (FIG. 5B) or barrel-type (FIG. 5C) conical structure.

Depending on the shape of the mirror 1112M, the width of the laser beam (i.e., "W" shown in FIG. 5A) can be properly adjusted, as it is reflected from the mirror's surface and sent to the surface of the specimen after passing through the array transducer 1112M. Therefore, the width of illumination can be optimized to accommodate the application purpose of the endoscope by varying the shape of the mirror 1112M.

For example, if a pincushion-type conical mirror 1112M-PC is utilized as is shown in FIG. 5B, wherein the side of the cone is curved inward, an illumination zone with a narrow width (W) can form on the surface of a specimen. However, if a barrel-type conical mirror 1112M-BR is used as shown in FIG. 5C, wherein the side of the cone is curved outward, an illumination zone with a wide width (W) can form on the surface of a specimen.

According to an embodiment, a light diffuser 1112 may include a beam shaper 1112BS that first deflects the laser beam delivered from an optical fiber 1113 to a transverse plane and also a prism 1112P that is located at the central region of the array transducer 1111 and that has a conically-dented reflection surface to evenly spread the laser beam transmitted from the beam shaper 1112BS radially in all directions.

Figure 5D:
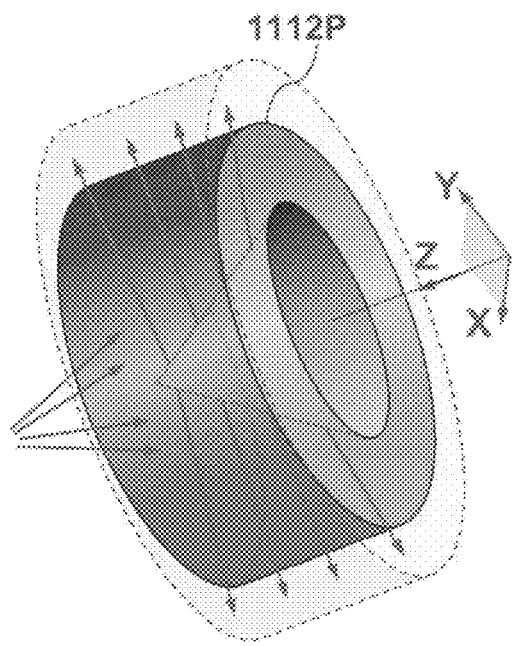

Referring to FIG. 5D, as opposed to the aforementioned mirror 1112M-based light reflection case, it is also possible to spread the laser beam radially in all directions by using a prism 1112P that has a conically-dented reflection surface. This would reflect the laser beam at the inner boundary of the conical surface of the prism 1112P based on the total internal reflection principle.

Since the prism 1112P is made from a typical optical substrate material, such as glass or quartz, has a columnar shape, and is given a conically-dented hole at one side (i.e., one of the two flat surfaces), it is possible to fully reflect an approaching laser beam from the other flat surface of the prism 1112P at the inner boundary of the conically-dented hole. This means that the desired light reflection and expansion effects also can be achieved, though an additional light reflection coating layer is not formed on the surface of the prism 1112P like a typical mirror. Moreover, if the rim of the prism is shaped like a cylindrical column, it is also possible to use the prism 1112P as an acoustic backing layer. This is because the prism 1112P has a cylindrical surface that can be placed in close contact with the ring-shaped array transducer 1111. Here, a backing layer refers to a layer that may increase the sensitivity of an array transducer by providing adequate acoustic impedance difference to the piezoelectric layer of the array transducer and also may function as a sound absorbing layer that takes in remnant photoacoustic or ultrasonic waves not perfectly captured by the array transducer 1111 as a desired electric signal. Other possible embodiments forming the backing layer are described later.

In FIG. 5D, only one example of a prism with a straight reflection side is illustrated. However, unlike the illustration, the conical reflection surface may also be formed in a curved inward or curved outward shape similar to the examples shown in FIGS. 5B and 5C. Depending on the shape of the prism 1112P, the width (W) of the illumination formed on the surface of the specimen by the laser beam propagating from the array transducer 1111 after it is reflected from the prism 1112P may vary. This means that the width of illumination can be optimized to meet the application purpose of the endoscope by varying the conical surface shape of the prism 1112P.

In FIG. 5D, only an example of a prism 1112P with a cylindrical outer surface is illustrated. However, the outer cylindrical side of the prism 1112P could be altered so that it is curved inward (i.e., a bottleneck shape) or curved outward (i.e., a barrel shape).

The above example shows an embodiment of a light diffuser 1112 including a mirror 1112M with a rotational symmetry with respect to the central axis of the endoscopic probe (i.e., Z-axis). However, the light diffuser 1112 does not necessarily require a rotationally symmetric shape, and could thus have different forms depending on varying application directions.

Figure 6:
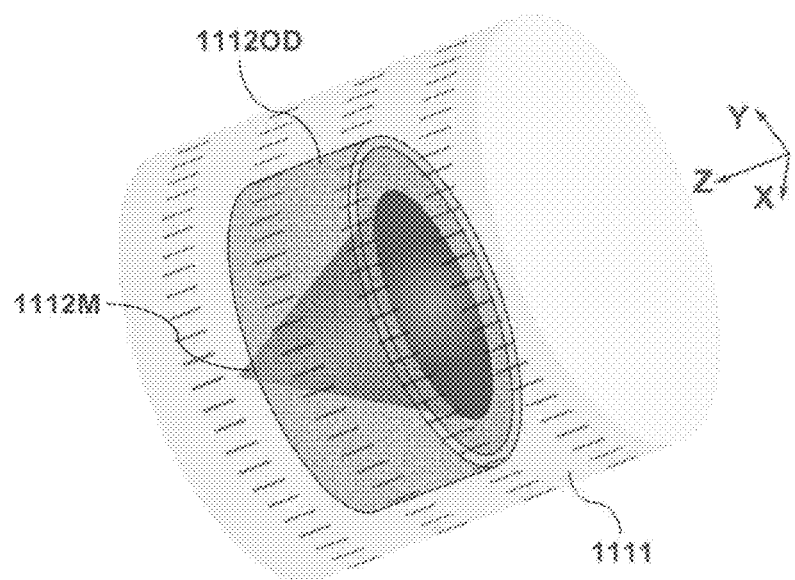
FIG. 6 is a view showing the shape and configuration of a light scattering layer added to make the laser beam reflected by a light diffuser diverge more uniformly according to an embodiment.

FIG. 6 is a view showing the shape and configuration of a light scattering layer which could be added to make the laser beam reflected by a light diffuser diverge more uniformly.

According to an embodiment, a light diffuser 1112 may further include a light scattering layer 1112OD, which would be placed inside an array transducer 1111 and would surround the outer side of the mirror 1112M.

Referring to FIG. 6, a light scattering layer 1112OD with a cylindrical or pipe-like shape and predetermined wall thickness is placed on the outer side of a mirror 1112M. That is, the light scattering layer 1112OD is placed in the scanning head 1110 so that its outer surface is in direct contact with the inner surface of the array transducer 1111. Inside the scanning head 1110, the light scattering layer 1112OD further homogenizes the laser beam diverging from the mirror 1112M showing an uneven intensity distribution. However, to make the light scattering layer 1112OD perform the aforementioned role more effectively, it is important to select the light scattering layer's substrate material with the appropriate optical properties. Here, the optical properties refer to the absorption coefficient $\mu_a$, the scattering coefficient $\mu_s$, and the anisotropy factor g, all of which are typically utilized for modeling light propagation phenomenon in biological tissues according to the theory of tissue optics.

According to an embodiment, the reduced scattering coefficient ($\mu_s'$) of the light scattering layer 1112OD may be equal to or greater than 0.1 cm$^{-1}$, and equal to or less than 1.0 cm$^{-1}$. Here, the reduced scattering coefficient ($\mu_s'$) is a parameter with the relationship $\mu_s'=\mu_s(1-g)$, wherein $\mu_s$ is the assigned scattering coefficient and g is the assigned anisotropy factor. For example, if a reduced scattering coefficient value of 4 cm$^{-1}$ is assumed, whenever a photon travels 0.25 cm (=¼ cm$^{-1}$), the photon would scatter omnidirectionally with the same probability. If the reduced scattering coefficient has a value of 0.1-1 cm$^{-1}$ (as it does in the present disclosure), the intensity distribution of the laser beam formed on the surface of a specimen would become more uniform. This is because the rays of the laser beam that pass through the light scattering layer 1112OD would be deflected slightly. In terms of selecting the material for the light scattering layer 1112OD, a plastic resin such as polypropylene, ground glass, and engineer diffuser could be used. However, the material is not limited to these options.

Meanwhile, it is desirable that the absorption coefficient ($\mu_a$) of the light scattering layer 1112OD has a value as close to zero as possible. This is because, if its absorption coefficient is not negligible, the scattering light diffuser 1112OD itself may absorb light and convert its energy into heat.

As mentioned above, the light scattering layer 1112OD plays a role in sending the laser beam dispersed by the mirror 1112M to the array transducer 1111 as evenly as possible without energy loss. In addition to the mentioned role, the light scattering layer 1112OD may also serve as an acoustic backing layer for the array transducer 1111.

Figure 7A:
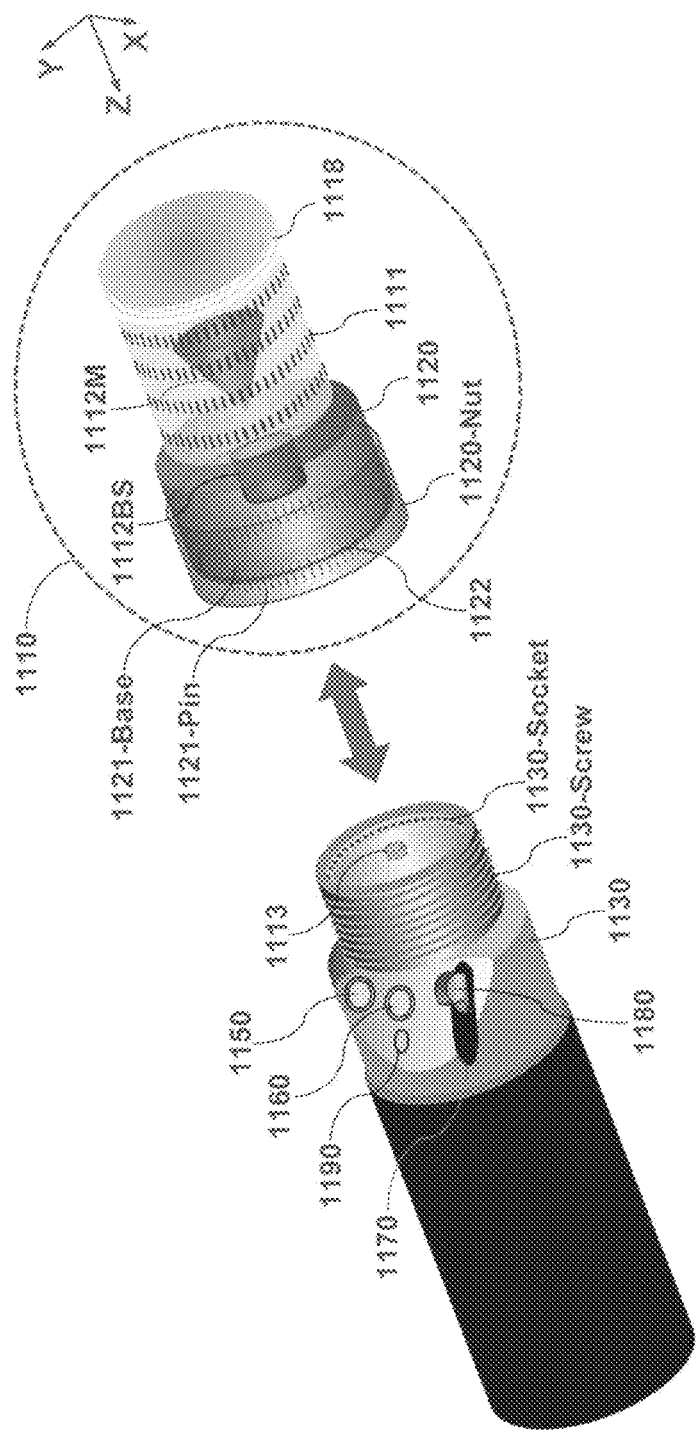
FIGS. 7A and 7B are schematic diagrams showing the structure of a detachable scanning head according to an embodiment.
Figure 7B:
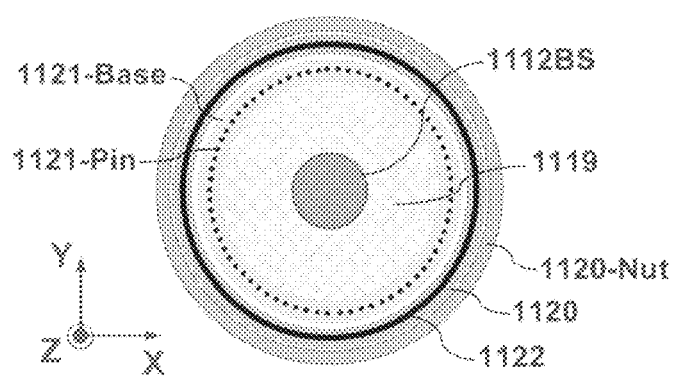

FIGS. 7A and 7B are schematic diagrams showing the structure of a detachable scanning head according to an embodiment.

The scanning head 1110 of the PAE-EUS probe 1000 according to the present disclosure can be implemented in a form that can also be separated from the endoscopic probe.

Referring to FIGS. 7A and 7B, the scanning head 1110 of the PAE-EUS probe 1000 can be separated from the endoscopic probe from a point located between the scan head support 1120 and the hose end frame 1130. In other words, the scanning head 1110 including the scan head support 1120 can be detached from the hose end frame 1130.

When the scanning head 1110 is separated from the endoscopic probe, the beam shaper 1112BS and the mirror 1112M may also be separated from the endoscopic probe. Alternatively, either the beam shaper 1112BS or the mirror 1112M can be separated from the endoscopic probe.

In the above instance, the formation of multiple conductive connection pins 1121-Pin at the lower part of the scanning head base frame 1120 may be required. Moreover, a connection socket 1130-Socket with the same number of pin holes corresponding to the total number of conductive connection pins 1121-Pin may need to be created at the distal end of the hose end frame 1130 in a protruding form. An electrical conduction path between the array transducer 1111 and the endoscopic probe can then be provided by the conductive connection pins 1121-Pin and the connection socket 1130-Socket. Through this mechanism, the scanning head 1110 can be removed from the endoscopic probe whenever necessary.

Meanwhile, the cable splitter 1115 which is illustrated in FIG. 2 and could also play such a role as pre-amplification or multiplexing may be included in the separable scanning head 1110. In this case, the electrical signals primarily processed in the cable splitter 1115 can be further transmitted to the electric wire bundle 1114 through the conductive connection pins 1121-Pin and the connection socket 1130-Socket.

FIG. 7B represents the structure of a scanning head 1110 viewed from the bottom, i.e., +Z-axis, according to an embodiment. As illustrated in FIGS. 7A and 7B, multiple conductive connection pins 1121-Pin electrically connected to the transducer elements of the array transducer 1111 may be distributed along the circular rim of an insulating base 1121-Base (made of a plastic resin, for example) in a predetermined pattern. In this instance, a waterproof O-ring 1122 may also be placed around the rim of the scanning head base frame 1120 and the outer surface of the insulating base 1121-Base to prevent the invasion of external fluids (such as water or body fluid) during an endoscopic procedure.

When the scanning head 1110 is connected to the endoscopic probe, the waterproof O-ring 1122 already mounted around the rim of the scanning head base frame 1120 is firmly engaged with the distal end of the screw-shaped ferrule (i.e., the rim part of the connection screw 1130-Screw) protruding from the hose end frame 1130 to the −Z-axis. With firm engagement, any external fluid cannot invade the conductive connection pins 1121-Pin, connection socket 1130-Socket, or optics, including the optical fiber 1113.

Meanwhile, the scanning head base frame 1120 and hose end frame 1130 may have an internally-threaded coupling nut 1120-nut and an externally-threaded connection screw 1130-Screw respectively. In this instance, it is possible to firmly fix the scanning head base frame 1120 to the hose end frame 1130 by inserting the conductive connection pins 1121-Pin into the connection socket 1130-Socket and turning the coupling nut 1120-Nut in the direction of the connection screw 1130-Screw.

Also, as shown in FIG. 7B, a transparent window 1119 made of glass or quartz may be installed at the central part of the insulating base 1121-Base that supports the conductive connection pins 1121-Pin. The transparent window 1119 may prevent foreign substances such as dust from entering the optics of the scanning head 1110 when the scanning head 1110 is detached.

By employing the mentioned conductive connection pins 1121-Pin and the connection socket 1130-Socket, it is possible to easily attach and detach the scanning head 1110 to and from the endoscopic probe. The related mechanisms, component shapes, and internal structures could be understood as those which are commonly used in the electronic components of devices, such as the central processing unit (CPU) of a personal computer. Also, the connection mechanism between the coupling nut 1120-nut, which is engaged with the scanning head base frame 1120 and the connection crew 1130-Screw, is very similar to that of the male and female SubMiniature version A (SMA) connectors or ultra-high frequency (UHF) connectors frequently used in the area of radio frequency (RF) communication.

The distribution pattern of the conductive connection pins 1121-Pin depicted in FIG. 7B is only an example and can be modified to reflect other forms, such as double rows or matrix-like arrangement, rather than the single row. Furthermore, the connection screw 1130-Screws joined to the hose end frame 1130 may also be designed as an integral, single-piece structure with the hose end frame 1130.

If the form of the endoscopic probe allows for the scanning head 1110 to be detachable, it is possible to keep the performance of the scanning head 1110 constant. This is because the scanning head 1110 can be replaced at any time. Moreover, this structure is advantageous in that the scanning head 1110 can be replaced with any other scanning head 1110 including an array transducer 1111 that has a different array pattern.

One of the main objectives of the present disclosure is to maximize both an LEA and a USA by arranging them to overlap each other, and consequently it has been proposed that such overlap can be achieved if an array transducer with optical transparency is employed. Hereinafter, several possible embodiments of such an optically-transparent array transducer 1111 are explained.

According to an embodiment, the optically-transparent array transducer 1111 may be comprised of a piezoelectric layer of a predetermined thickness, a group of first electrodes arranged on a surface of the piezoelectric layer in a one-dimensional (1D) or 2D fashion, and a group of second electrodes arranged on the other surface of the piezoelectric layer in parallel to the first electrodes. In the described embodiment, possible examples of a piezoelectric material that could be used for the piezoelectric layer may include a type of polymer, ceramics, and a single crystal, and, in forming the array transducer 1111, the piezoelectric layer itself may be placed as a continuous single piece or as several separate pieces. The manner in which a continuous single piezoelectric layer in an array transducer 1111 is possible will be addressed later.

Figure 8:
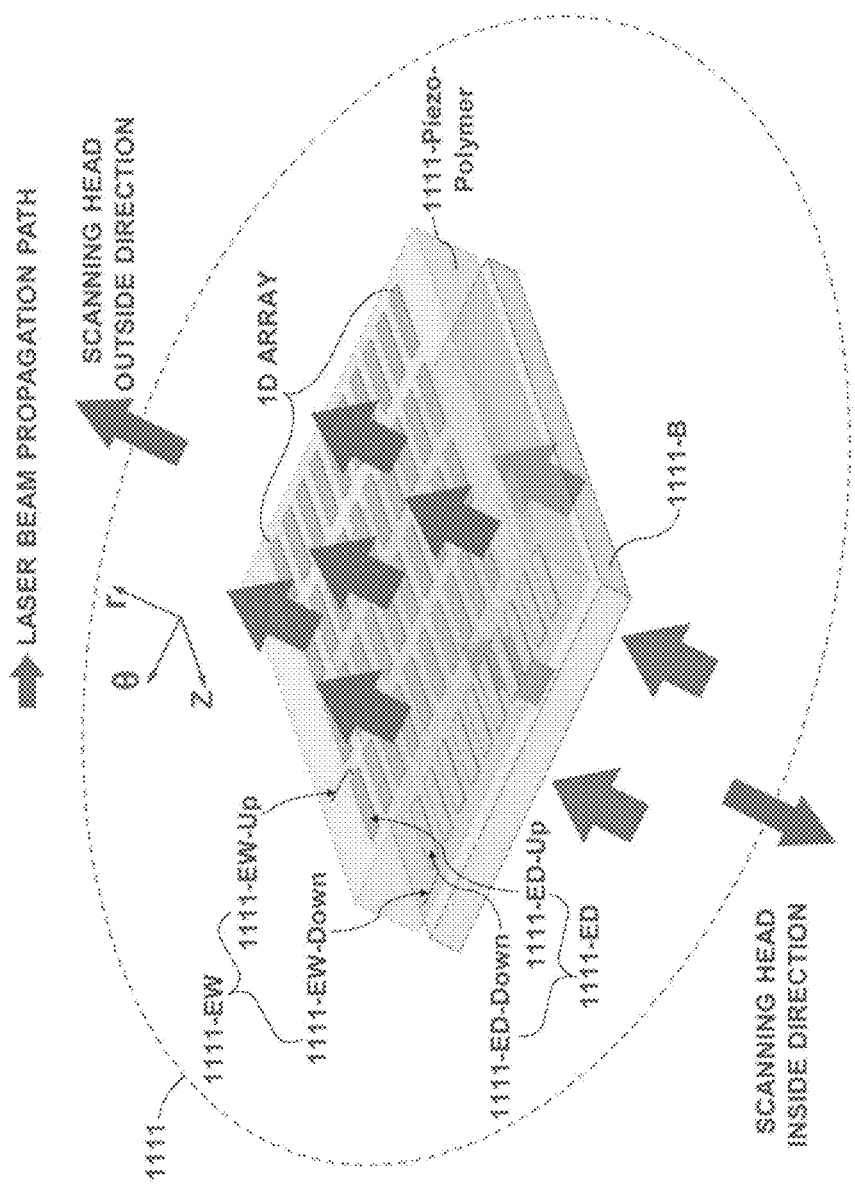
FIG. 8 is a schematic diagram illustrating the structure of a portion of the optically-transparent array transducer implemented using piezoelectric polymer film and transparent electrodes according to an embodiment.

FIG. 8 is a schematic diagram illustrating the structure of an optically-transparent array transducer 1111 implemented using piezoelectric polymer film and transparent electrodes according to an embodiment. The diagram represents only a small portion of the entire USA of the ring-shaped array transducer 1111 distributed around the scanning head depicted in a flattened, unrolled style.

As shown in FIG. 8, a piezoelectric polymer film 1111-Piezo-Polymer is located between the first electrodes 1111-ED-Up and the second electrodes 1111-ED-Down. That is, FIG. 8 illustrates a case in which the piezoelectric layer is made of a piezoelectric polymer film 1111-Piezo-Polymer. In this case, it is preferable that the polymer-based piezoelectric material has such an optical property that light waves can easily pass through it. Thus, possible examples of the piezoelectric material that satisfy this condition may include polyvinylidene fluoride (PVDF) and poly[(vinylidenefluoride-co-trifluoroethylene)] P(VDF-TrFE), which is a copolymer of PVDF.

In general, it is well known that, since a polymer-based piezoelectric material has a lower electromechanical coupling coefficient (k) than that of a ceramic-based piezoelectric material, the polymer-based piezoelectric material has relatively low energy efficiency. Here, the electromechanical coupling coefficient (k) refers to the conversion efficiency of mechanical energy to electric energy. Thus, if the k-value of a piezoelectric material is low, for example, the maximum signal sensing depth of the related ultrasonic sensor is also low for a given unit electrical energy input. However, the polymer-based piezoelectric material exhibits very high electrode-voltage response characteristics for a unit physical deformation because the total electric charges induced by a unit deformation at an electrode are relatively low due to its low dielectric permittivity ($\varepsilon$). Thus, if a pre-amplifier with an adequate electrical input impedance matching the output impedance of the polymer-based piezoelectric sensor is employed, signal sensitivity comparable to that of a ceramic sensor could be achieved.

Leaving aside the mentioned advantage, since the key objective of the present disclosure is to provide an advanced PAE-EUS probe structure with a more enhanced PAI capability rather than an ultrasound imaging capability, such a low electromechanical coupling coefficient of a piezoelectric polymer film may not be a big issue. This is true because, unlike conventional ultrasound imaging, which requires two electromechanical conversion processes, including the ultrasonic pulse emission to an object to be examined through the first electro-mechanical conversion and the detection of reflected acoustic waves after a predetermined time interval through the second mechano-electrical conversion, PAI only requires one mechano-electrical conversion process. That is, since only one mechano-electrical conversion process is involved in PAI, and also the maximum imaging depth of a PAI system is mainly determined by the optical illumination parameters, as described above, the relatively low electromechanical coupling coefficient value of a polymer-based piezoelectric material is not a big concern.

In addition to the explained electrical characteristics, a polymer-based piezoelectric sensor also has other advantages; it is inexpensive, it is flexible, and its sub-elements, such as electrodes or electric wires, may be easily formed in a desired pattern on its surface.

Referring back to FIG. 8, the array transducer 1111 may include a number of first electrodes 1111-ED-Up and second electrodes 1111-ED-Down, which are formed on both surfaces of the piezoelectric polymer film 1111-Piezo-Polymer with a predetermined thickness. That is, the piezoelectric polymer film 1111-Piezo-Polymer acts as a kind of a wafer, and the first electrodes 1111-ED-Up and the second electrodes 1111-ED-Down are formed in parallel so that each pair can function as one unit of ultrasonic sensor element.

Here, the electrodes 1111-ED, including a number of first electrodes 1111-ED-Up and second electrodes 1111-ED-Down, may be arranged in a 1D linear or 2D planar pattern. That is, multiple pairs of electrodes 1111-ED formed on both surfaces of the piezoelectric polymer film 1111-Piezo-Polymer, like a parallel-plate, may be arranged along the Y-axis to form a 1D array, and, if necessary, additional groups of 1D arrays may be expanded along the X-axis to form a 2D array. In this case, since the center frequency ($f_c$) of the array transducer 1111 is mostly determined by the thickness of the piezoelectric polymer film 1111-Piezo-Polymer, and because the sound receiving angle of each element, through which an ultrasonic beam approaches the element, and the sensitivity of each element are mostly determined by X- and Y-axis widths of electrodes, the thickness of the piezoelectric polymer film 1111-Piezo-Polymer and the X and Y-widths of the electrodes have to be carefully determined, depending on the acoustic performance desired.

According to an embodiment, the first electrodes 1111-ED-Up and the second electrodes 1111-ED-Down may be optically-transparent.

If the electrodes 1111-ED formed on both surfaces of the piezoelectric polymer film 1111-Piezo-Polymer are made of an optically-transparent material, as mentioned above, the laser beam approaching from the light diffuser 1112 can pass through the electrodes 1111-ED without energy loss; consequently, the LEA can be maximized within the limited size of the scanning head 1110. In this case, the electric wires 1111-EW, which deliver the input/output current to/from the electrodes 1111-ED, must also be optically-transparent; to satisfy these requirements, the electrodes 1111-ED and the electric wires 1111-EW can be made of any of the following materials or related material groups: indium tin oxide (ITO), indium zinc oxide (IZO), zinc oxide (ZnO), indium oxide ($In_2O_3$), Ge-doped $In_2O_3$ (IGO), and aluminum-doped zinc oxide (AZO), or any other materials with the mentioned characteristics.

That is, since the electric wires 1111-EW, the electrodes 1111-ED, and the piezoelectric polymer film 1111-Piezo-Polymer included in the array transducer 1111 are all optically-transparent, the laser beam diffused by the light diffuser 1112 can be delivered to the object to be examined over the entire area where the array transducer 1111 spans.

The PAE-EUS system according to an embodiment may further include a sub-unit in the system console 4000 or a related function that processes a set of detected photoacoustic and ultrasonic signals to produce a PAE-EUS image, and the sub-unit or the related function may also play a role that removes the image artifacts occurred due to the photoacoustic waves generated by the first electrodes 1111-ED-Up and the second electrodes 1111-ED-Down.

Although the first electrodes 1111-ED-Up and the second electrodes 1111-ED-Down are optically-transparent, their absorption coefficients may not be perfectly zero (0), in reality; thus, they may absorb some amount of the laser energy, which resultantly generates unwanted photoacoustic waves. The unwanted photoacoustic waves may be mixed with the normal photoacoustic waves generated in the object to be examined at the same moment; thus, they may be detected together as a signal, and may appear as an artifact in an obtained image.

If the mentioned image artifacts are not negligible, they could be removed through an appropriate deconvolution process using the ultrasonic image information that can be provided by the present endoscopic system along with the photoacoustic image information, after carefully analyzing how the image artifacts are intervened into an obtained photoacoustic image in advance. The reason why those image artifacts could be filtered in this way is that the corresponding unwanted photoacoustic signals detected by the array transducer 1111, i.e., the photoacoustic waves generated by the transparent electrodes and then detected by the array transducer 1111 after being reflected from the object, is very similar to the ultrasonic pulse-echo signals acquired according to a specific ultrasound imaging mode (for example, the simultaneous excitation mode of all the transducer elements, i.e., parallel beamforming), in terms of the morphological pattern recorded in an image. Hence, as suggested in Prior Document 17, while photoacoustic image data are continuously recorded, if the mentioned specific ultrasound imaging mode is performed between every two successive photoacoustic image frames (i.e., the photoacoustic and the ultrasound image data are recorded alternately), the obtained ultrasound image information could be utilized as deconvolution data in a subsequent image processing procedure.

The PAE-EUS probe according to an embodiment may further include a backing layer 1111-B that is also transparent and is located between the light diffuser 1112 and the piezoelectric polymer film 1111-Piezo-Polymer. That is, as shown in FIG. 8, the backing layer 1111-B can be placed right underneath the piezoelectric polymer film 1111-Piezo-Polymer (i.e., the r→0 direction). Thus, the laser beam propagating from a light diffuser can freely pass through the backing layer 1111-B because the backing layer 1111-B is also transparent.

According to another embodiment, the backing layer 1111-B shown in FIG. 8 may be integrated with the light scattering layer 1112OD shown in FIG. 6 as a single unit. That is, in this case, the light scattering layer 1112OD may function as a backing layer as well as a sound absorbing layer. For example, a light scattering layer 1112OD that exhibits these characteristics could be implemented by adding acoustic scatterers and sound absorbers, such as epoxy or silica particles, into a light-diffusing material that serves as a substrate.

Figure 9:
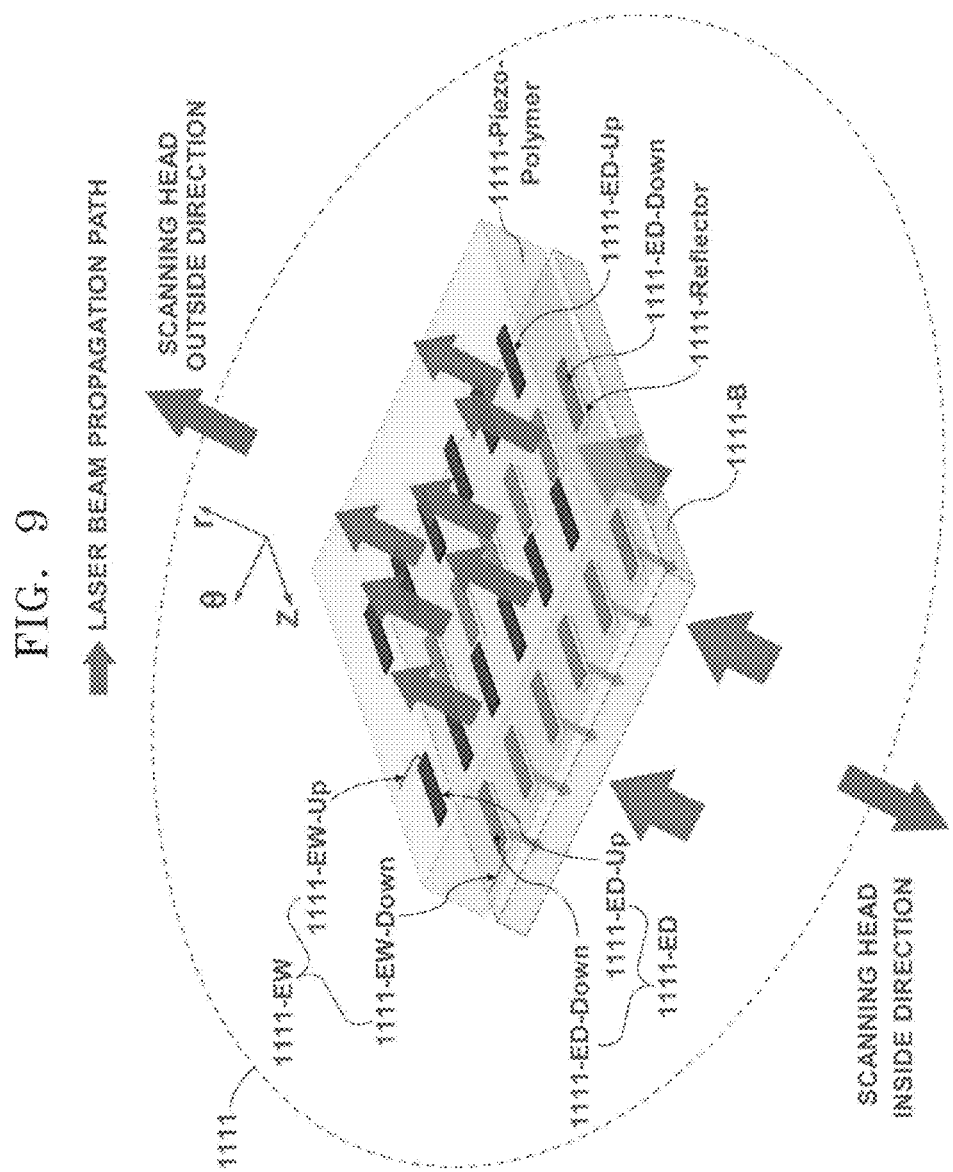
FIG. 9 is a schematic diagram illustrating the structure of a portion of the optically-transparent array transducer implemented using a piezoelectric polymer film and non-transparent electrodes according to an embodiment.
Figure 10A:
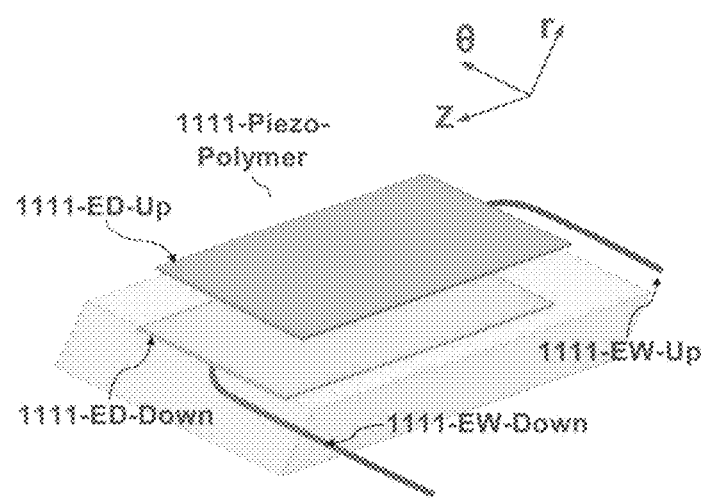
FIGS. 10A through 10D are views illustrating the input and output structures of the electric wires connected to each of the transducer elements of an array transducer according to an embodiment.
Figure 10B:
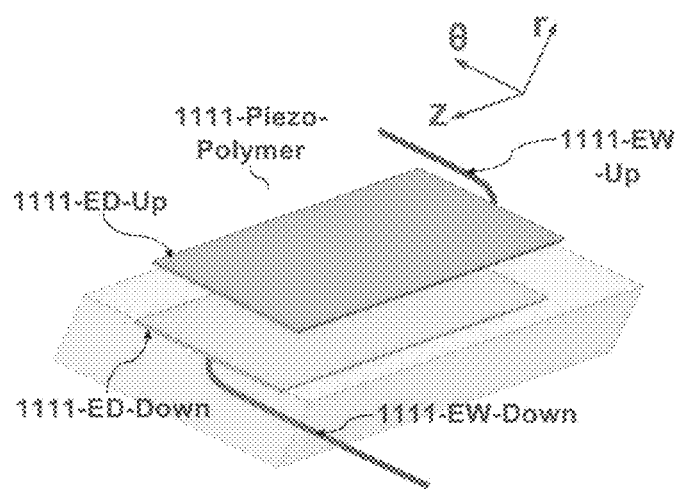
Figure 10C:
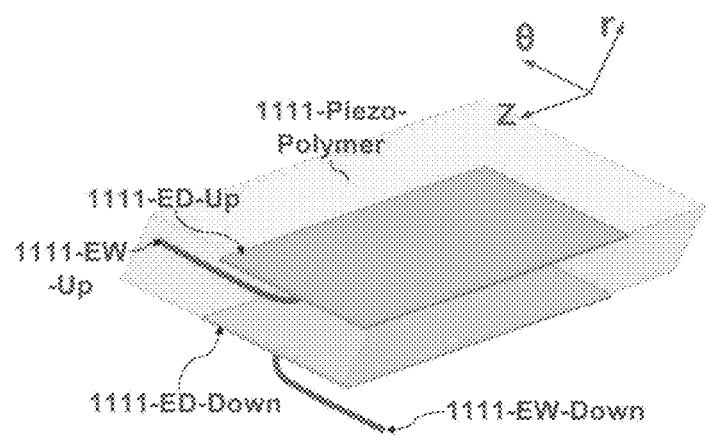
Figure 10D:
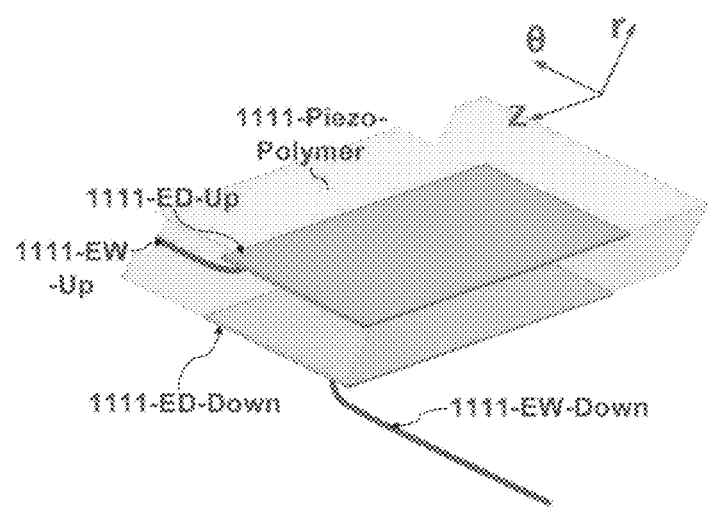

FIG. 9 is a schematic diagram illustrating the structure of a portion of the optically-transparent array transducer 1111 implemented using a piezoelectric polymer film and non-transparent electrodes according to an embodiment.

According to an embodiment, the multiple first electrodes 1111-ED-Up and the multiple second electrodes 1111-ED-Down may be formed using non-transparent electrodes.

Referring to FIG. 9, the electrodes 1111-ED may be non-transparent. In this case, the intervals between the first electrodes 1111-ED-Up and the intervals between the second electrodes 1111-ED-Down may be increased appropriately in order to provide an optical path through which a laser beam can freely pass. That is, although the electrodes 1111-ED are non-transparent, since the piezoelectric polymer film 1111-Piezo-Polymer itself is transparent, a laser beam can be transmitted through the portion where no electrode is distributed; thus, a partial transmission effect still can be achieved along the entire span area of the array transducer 1111.

Of course, in this case, an effective LEA may be reduced by the amount of area occupied by non-transparent electrodes. However, even in this case, a considerable amount of light energy can still be delivered through the LEA. For example, if only half the number of the electrodes shown in FIG. 8 are formed in an array transducer 1111, and all of them are formed as non-transparent electrodes (in which case, the spacing between the electrodes will be increased, as shown in FIG. 9), about half of the energy corresponding to the design where all electrodes depicted in FIG. 8 are transparent can still be transmitted.

In addition to the loss of the LEA, a performance degradation, such as lateral resolution degradation due to the loss of an USA, may be a concern. However, even in this embodiment (i.e., FIG. 9), since the total span area of all the transducer elements is not reduced, in comparison to the case depicted in FIG. 8 (that is, the maximum viewing angle for a point object formed by all the transducer elements is still the same), the lateral resolution does not deteriorate significantly.

According to an embodiment, a light reflection layer 1111-Reflector may be located between the second electrodes 1111-ED-Down and a light diffuser 1112. Referring to FIG. 9, if the electrodes 1111-ED are non-transparent electrodes, the light reflection layers 1111-Reflector may also be placed right underneath the second electrodes 1111-ED-Down (i.e., the r→0 direction). In this case, the light reflection layers 1111-Reflector prevent a laser beam from entering the electrodes 1111-ED. If no light reflection layer 1111-Reflector is provided, some amount of the laser beam may be absorbed by the electrodes 1111-ED due to the non-transparent characteristics of those electrodes; thus, the unwanted photoacoustic waves, which would act later as acoustic noise or image artifacts, may be generated by the electrodes 1111-ED. Hence, if the light reflection layers 1111-Reflector are formed right underneath the second electrodes 1111-ED-Down, as shown in FIG. 9, the problem mentioned above can be prevented, and a laser beam approaching the light reflection layer 1111-Reflector may be reflected back to the light diffuser 11112 and can be recycled.

As described above, in the embodiments shown in FIGS. 8 and 9, an array transducer 1111 is implemented by arranging multiple electrodes on both surfaces of the piezoelectric polymer film 1111-Piezo-Polymer. That is, although only a single piece of the piezoelectric polymer film 1111-Piezo-Polymer is employed, and it extends over the entire span area of the USA or the LEA like a wafer, due to the multiple electrodes 1111-ED formed on both surfaces of the piezoelectric polymer film 1111-Piezo-Polymer with a predetermined width and interval, it (or they) can function as an array transducer.

However, one important thing that should be noted here is that only the two electrodes 1111-ED that are placed at each side of the piezoelectric polymer film 1111-Piezo-Polymer and face each other, like a parallel-plate structure, can form a sensor pair unit that functions as a transducer element. In other words, if there is any spot where any two pieces of electrically-conducting materials face each other at the points located at opposite sides of the piezoelectric polymer film 1111-Piezo-Polymer, the spot can also function as an ultrasonic signal sensing area. Accordingly, electric wires connected to each transducer element have to be carefully designed and arranged.

FIGS. 10A through 10D are views illustrating the input and output structure of the electric wires connected to each of the transducer elements of an optically-transparent array transducer 1111 according to an embodiment. Although the illustrated electric wire connections look random, there is a common rule that an electric wire 1111-EW-Up connected to the first electrode 1111-ED-Up and an electric wire 1111-EW-Down connected to the second electrode 1111-ED-Down should not face each other.

Until now, several embodiments of an optically-transparent array transducer 1111, which can be implemented using a piezoelectric polymer film 1111-Piezo-Polymer, have been described, and, in the presented embodiments, it can be seen that only a single piece of piezoelectric polymer film, which spans the entire area of an USA or LEA, is employed as a piezoelectric layer. However, according to the present disclosure, an array transducer can also be embodied by using multiple pieces of piezoelectric polymer films, which are placed piecewise inside the array transducer (the related figure is not shown).

According to another embodiment of the present disclosure, the piezoelectric layer of an array transducer 1111 may be formed from a ceramic material or a single crystal-based piezoelectric material that is frequently utilized in an existing ultrasound imaging instrument. In the current ultrasound imaging field, representative examples of a ceramic-based piezoelectric material include lead zirconate titanate (PZT) and barium titanate, and representative examples of a single crystal-based piezoelectric material include lithium niobate ($LiNbO_3$) and lead magnesium niobate-lead titanate (PMN-PT) (hereinafter, the term "ceramic" and "single crystal" are all encompassed as "crystal").

In general, realizing an array transducer required for the present disclosure by using a crystal-based piezoelectric material may not be as simply as the case using the piezoelectric polymer film 1111-Piezo-Polymer because crystal-based piezoelectric materials do not have high optical transparency or high flexibility in comparison to polymer-based piezoelectric materials. However, even with the crystal-based piezoelectric materials, an array transducer that satisfies the described requirements can be formed by manufacturing individual transducer elements first and then arranging them in predetermined positions.

Figure 11:
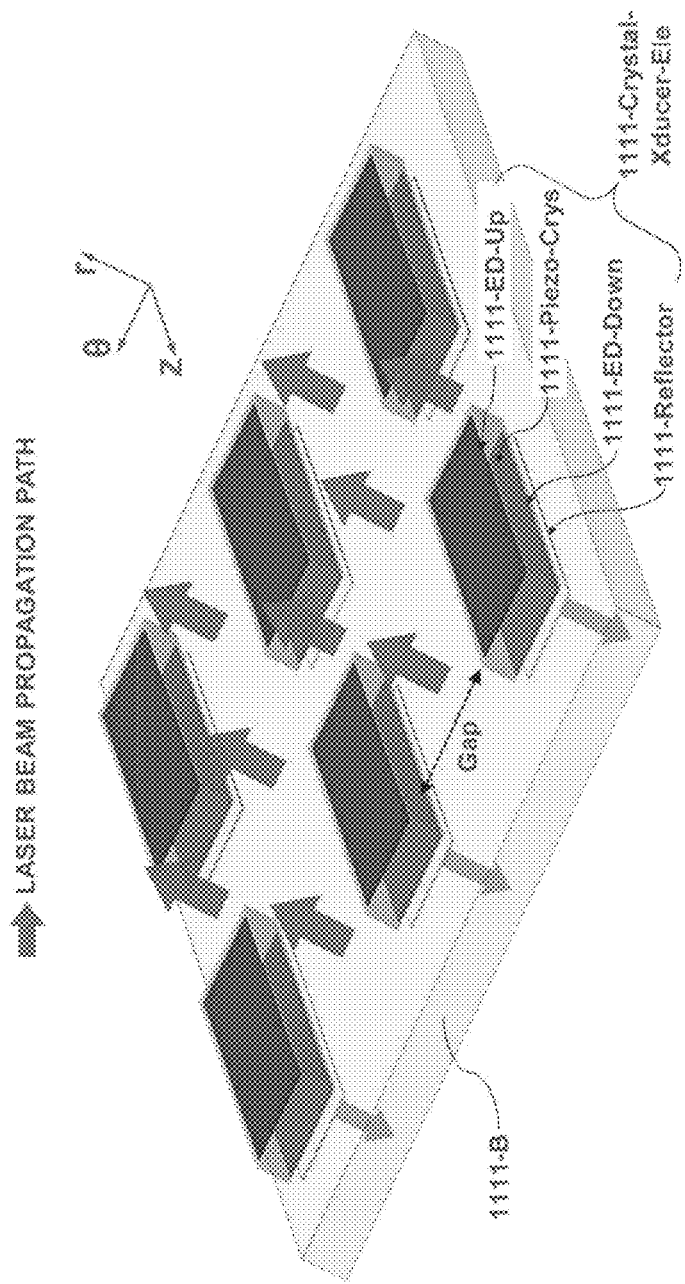
FIG. 11 is a schematic diagram illustrating the structure of a portion of the optically-transparent array transducer implemented using ceramic or single crystal-based piezoelectric material according to an embodiment.

FIG. 11 is a schematic diagram illustrating the structure of a portion of the optically-transparent array transducer 1111 implemented based on the mentioned manufacturing process according to an embodiment.

Referring to FIG. 11, multiple crystal-based transducer elements 1111-Crystal-Xducer-Ele, in which the electrodes 1111-ED and the electric wires 1111-EW (not shown) are pre-formed on both surfaces of a piezoelectric crystal 1111-Piezo-Crys with piezoelectricity (i.e., prior machined), are arranged on the backing layer 1111-B, which is also optically-transparent, at predetermined intervals to form an array transducer 1111. That is, even in this case, a laser beam propagating toward a target object to be examined can pass through the space (i.e., gaps) formed between the individual crystal-based transducer elements 1111-Crystal-Xducer-Ele, as seen in the case presented in FIG. 9 (i.e., a partially transparent array transducer is formed). In this case, the gaps between the crystal-based transducer elements 1111-Crystal-Xducer-Ele could be filled with the same material utilized to form the acoustic matching layer 1117 (e.g., TPX), or the gaps could be filled with another material. However, it is preferable that the type of material used to fill the gap be transparent.

Moreover, in this embodiment (i.e., FIG. 11), light reflection layers 1111-Reflector may be added right underneath the second electrodes 1111-ED-Down (i.e., the r→0 direction), as the case shown in FIG. 9, in order to prevent a laser beam from penetrating and passing through the second electrodes 1111-ED-Down.

Furthermore, in this embodiment, a backing layer 1111-B that functions as a base (substrate) for affixing the crystal-based transducer elements 1111-Crystal-Xducer-Ele, as well as a sound absorber may be added. In addition, the backing layer 1111-B may enable the crystal-based transducer elements 1111-Crystal-Xducer-Ele to exhibit maximum sensitivity performance by having an appropriate acoustic impedance difference in comparison to the piezoelectric crystals 1111-Piezo-Crys.

According to another embodiment, the backing layer 1111-B may be integrally formed with a light scattering layer 1112OD (that is, the light scattering layer 1112OD itself may function as a backing layer as well as a sound absorbing layer). In this case, all the crystal-based transducer elements 1111-Crystal-Xducer-Ele are directly attached to a surface of the light scattering layer 1112OD.

Figure 12:
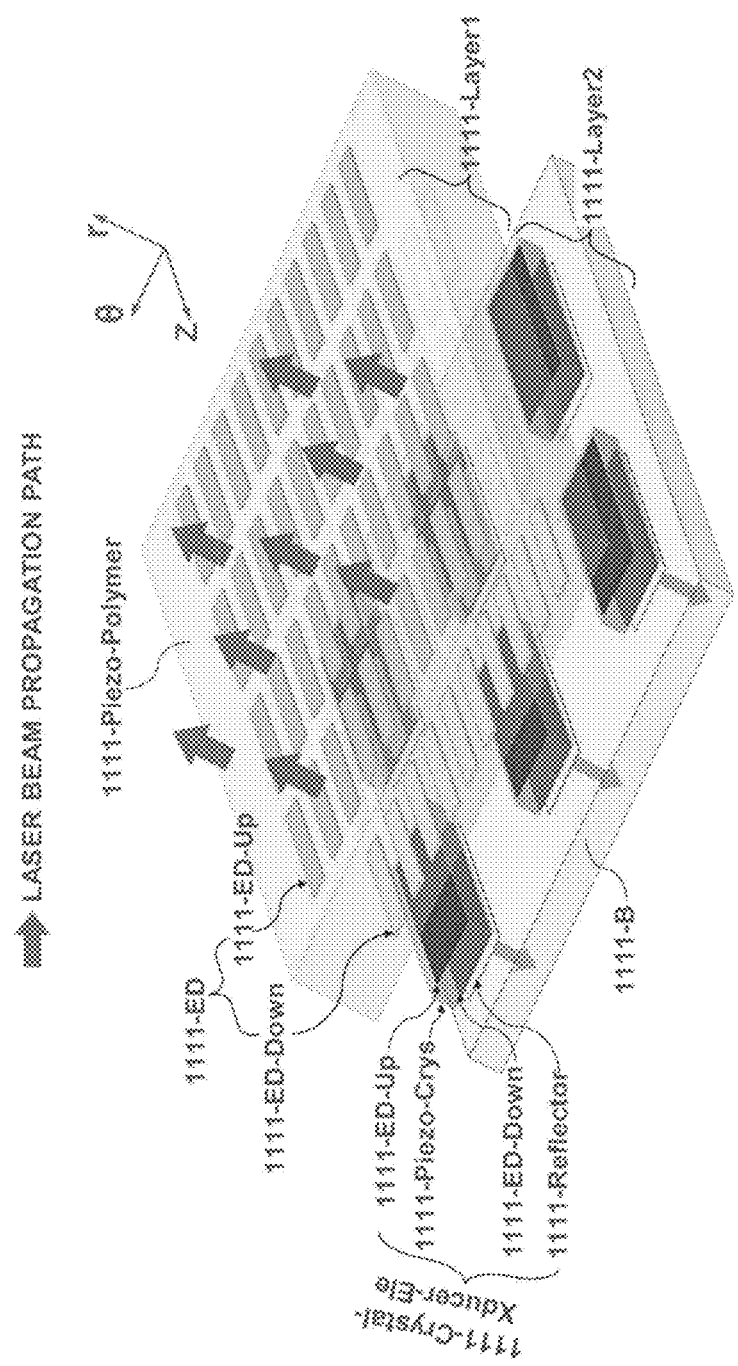
FIG. 12 is a schematic diagram illustrating the structure of a portion of the optically-transparent array transducer embodied by combining a ceramic or single crystal-based piezoelectric material with a polymer-type piezoelectric material according to an embodiment.

FIG. 12 is a schematic diagram illustrating the structure of a portion of the optically-transparent array transducer embodied by combining a ceramic or single crystal-based piezoelectric material with a polymer-type piezoelectric material. According to an embodiment, the optically-transparent array transducer 1111 can also be implemented in a hybrid form combining a ceramic or single crystal-based piezoelectric material with a polymer-based piezoelectric material (hereinafter, the term "crystal" encompasses both "ceramic" and "single crystal" as before).

Referring to FIG. 12, an optically-transparent array transducer 1111 according to an embodiment may include a first array transducer layer 1111-Layer1 implemented by using a crystal-based piezoelectric material, and a second array transducer layer 1111-Layer2 positioned on the outer surface of the first array transducer layer 1111-Layer1 and implemented by using a polymer-based piezoelectric material. That is, the optically-transparent and ring-shaped array transducer 1111 according to this embodiment may be embodied in a structure that the outer surface of the crystal-based first array transducer layer 1111-Layer1 is surrounded by the polymer-based second array transducer layer 1111-Layer2.

As previously explained, a polymer-based piezoelectric material is advantageous in the aspects that it exhibits higher electrode-voltage response characteristics for a unit physical deformation and has an acoustic impedance much closer to biological tissue when compared to crystal-based piezoelectric materials. Furthermore, the high optical transparency of the polymer itself, as well as the easiness of its electrode patterning, may act as an additional advantage when the manufacturing process of such an optically-transparent array transducer 1111 is considered. In contrast, crystal-based piezoelectric materials are more efficient than polymer-based piezoelectric materials in terms of energy efficiency, as they have higher electromechanical coupling coefficients (k), and exhibit more stable performances due to their relatively high Curie temperatures.

Thus, to compensate for the shortcomings of crystal-based and polymer-based piezoelectric materials, it is possible to implement a hybrid array transducer 1111 that combines the advantages of both materials. This could be done by placing a crystal-based first array transducer layer 1111-Layer1 inside the polymer-based second array transducer layer 1111-Layer2. An example of this hybrid array transducer 1111 is shown in FIG. 12, where the first array transducer layer 1111-Layer1 and the second array transducer layer 1111-Layer2 have the same structures as shown in FIGS. 8 and 11, respectively. In this case, the first array transducer layer 1111-Layer1 with a low acoustic impedance may act as the acoustic matching layer of the second array transducer layer 1111-Layer2, whereas the second array transducer layer 1111-Layer2 with a high acoustic impedance may act as the backing layer for the first array transducer layer 1111-Layer1.

In the first or second array transducer layers (1111-Layer1 or 1111-Layer2) depicted in FIG. 12, the suggested position, number, and spacing of the electrodes 1111-ED are only for illustrative purposes and can be appropriately determined according to a desired application direction and performance. Further, the thickness of the piezoelectric polymer film 1111-Piezo-Polymer can be chosen appropriately with respect to the ultrasonic frequency range to be detected.

Until now, several embodiments of the optically-transparent array transducer 1111 have been described. Herein, the cross-sectional structure of the insertion hose shown in FIG. 1 and an acoustic matching method between the scanning head and a specimen, as in the case shown in FIG. 3, will be described.

Figure 13:
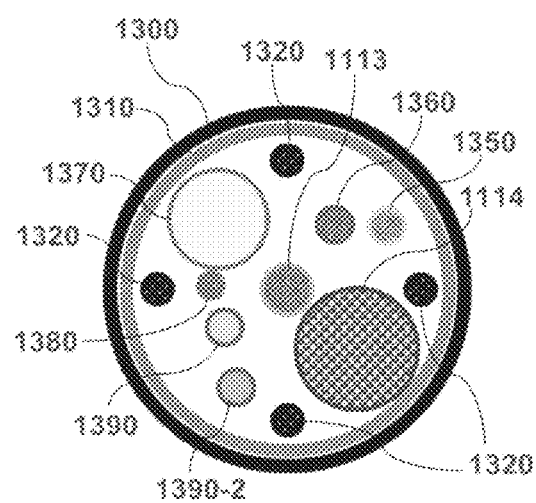
FIG. 13 is a view illustrating the cross-sectional structure of the insertion hose of a photoacoustic-ultrasonic endoscopic probe according to an embodiment.

FIG. 13 is a view illustrating the cross-sectional structure of the insertion hose of a PAE-EUS probe according to an embodiment.

Referring to FIGS. 13, 1, and 2, a metal mesh 1310 with a braided or coil-like structure may be placed just inside the wall of the insertion hose 1300 of the PAE-EUS probe. The metal mesh 1310 allows the insertion hose 1300 to be freely bent while maintaining a predetermined shape that prevents it from shrinking, thus protecting the various elements that pass through the metal mesh 1310. Also, the metal mesh 1310 protects internal circuits and electric wires from external electromagnetic noise. Thus, to meet the explained functional requirement, the metal mesh may consist of multiple layers, not a single wire.

Inside the metal mesh 1310, angulation wires 1320—which allow the angulation section 1200, illustrated in FIG. 1, to be bent in any direction—may be placed. The angulation wires 1320 consist of two sets of paired wires facing each other relative to the central axis of the endoscopic probe; if one wire pushes one side of the distal section 1100, the opposite wire pulls the opposite side, and thus the angulation section 1200 (which supports the distal section 1100) can be bent in any direction. The push and pull of these angulation wires 1320 can be manipulated by the two direction control knobs 1500-1 and 1500-2, as illustrated in FIG. 1.

Near the center of the insertion hose 1300, a single strand or multiple strands of optical fiber 1113 may be positioned to transmit the laser pulse required for PAI. Around the optical fiber 1113, an electric wire bundle 1114 connected to each piezoelectric element of the array transducer 1111 directly or via the cable splitter 1115, and an accessory channel 1370 which connects the accessory channel inlet 1600 to the accessory channel outlet 1170 and through which a variety of biopsy tools may pass may be positioned. Around the accessory channel 1370, a biopsy needle lever wire 1380 (required to operate the biopsy needle lever 1180) may be placed.

Additionally, a water channel 1390 (which can deliver water to be ejected through the waterjet nozzle 1190), an air channel 1390-2 (which can transport the air to be ejected through an air jet nozzle [not shown]), a camera signal cable 1350 (which transmits the electric signal captured by the small CCD camera 1150 to the proximal part of the endoscopic probe), and a visual-field illumination unit cable 1360 (which transmits electric power and control signals to the visual-field illumination unit 1160, located inside the hose end frame 1130) may be positioned inside the metal mesh 1310. If the visual-field illumination unit 1160 is something like a device that illuminates specimens by guiding light from outside of the endoscopic probe (e.g., the system console 4000) rather than a light-emitting diode (LED) or a lamp, the described visual-field illumination unit cable 1360 may need to be replaced with an optical fiber cable.

Figure 14:
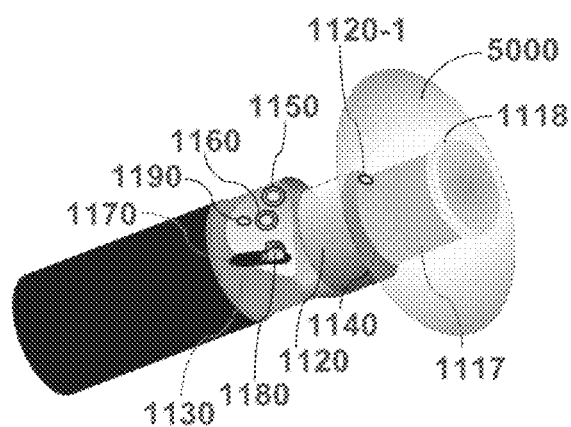
FIG. 14 is a view illustrating an exemplary embodiment of a balloon installed on an end of a photoacoustic-ultrasonic endoscopic probe in order to solve an acoustic matching problem between an object to be examined and the endoscopic probe during an endoscopic imaging procedure.
Figure 15A:
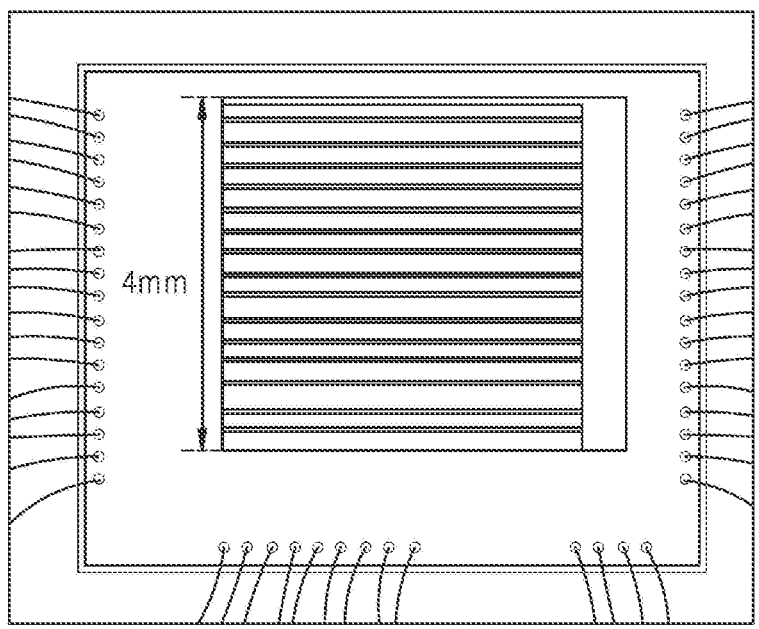
Figure 15B:
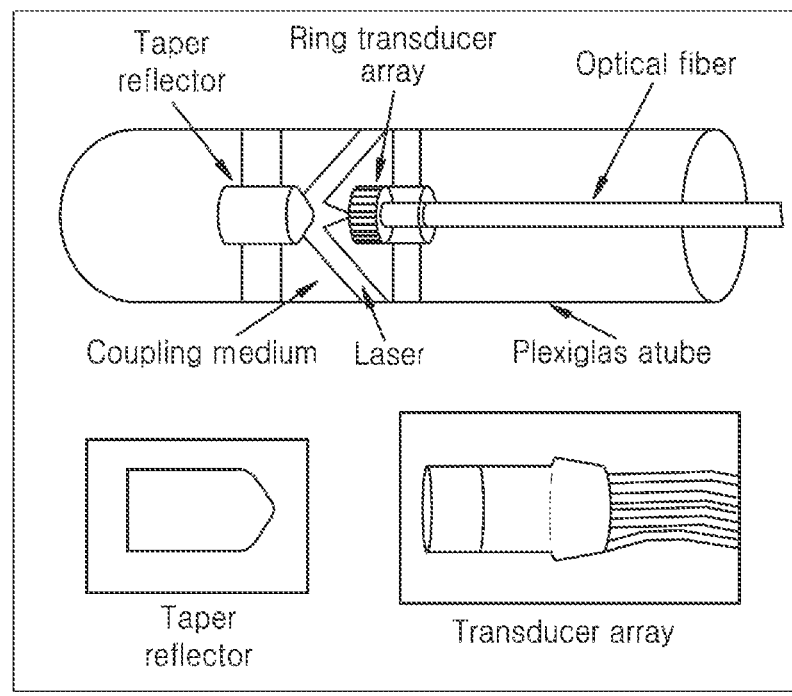
Figure 16A:
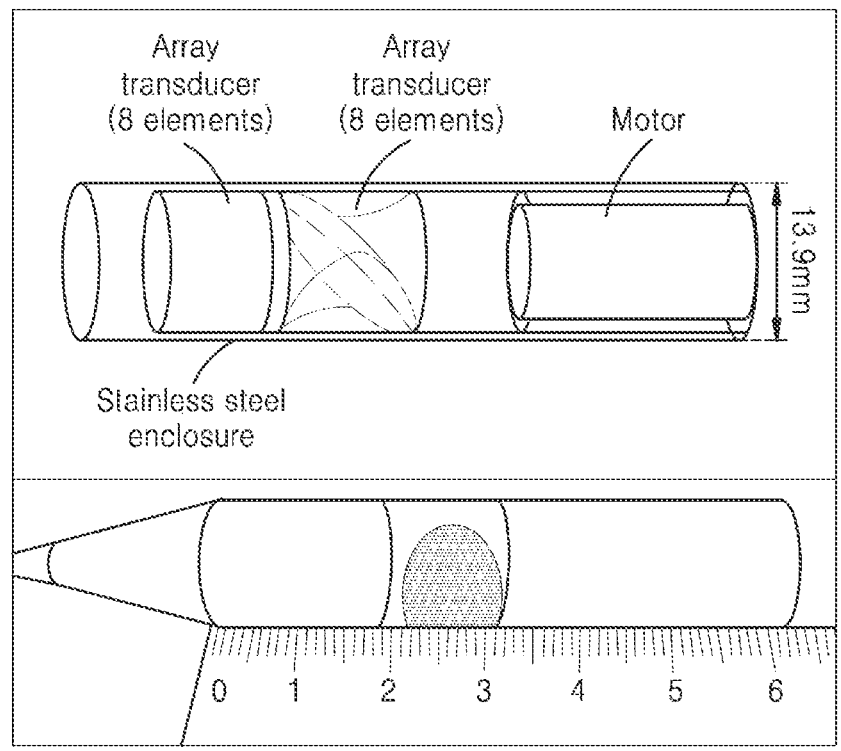
Figure 16B:
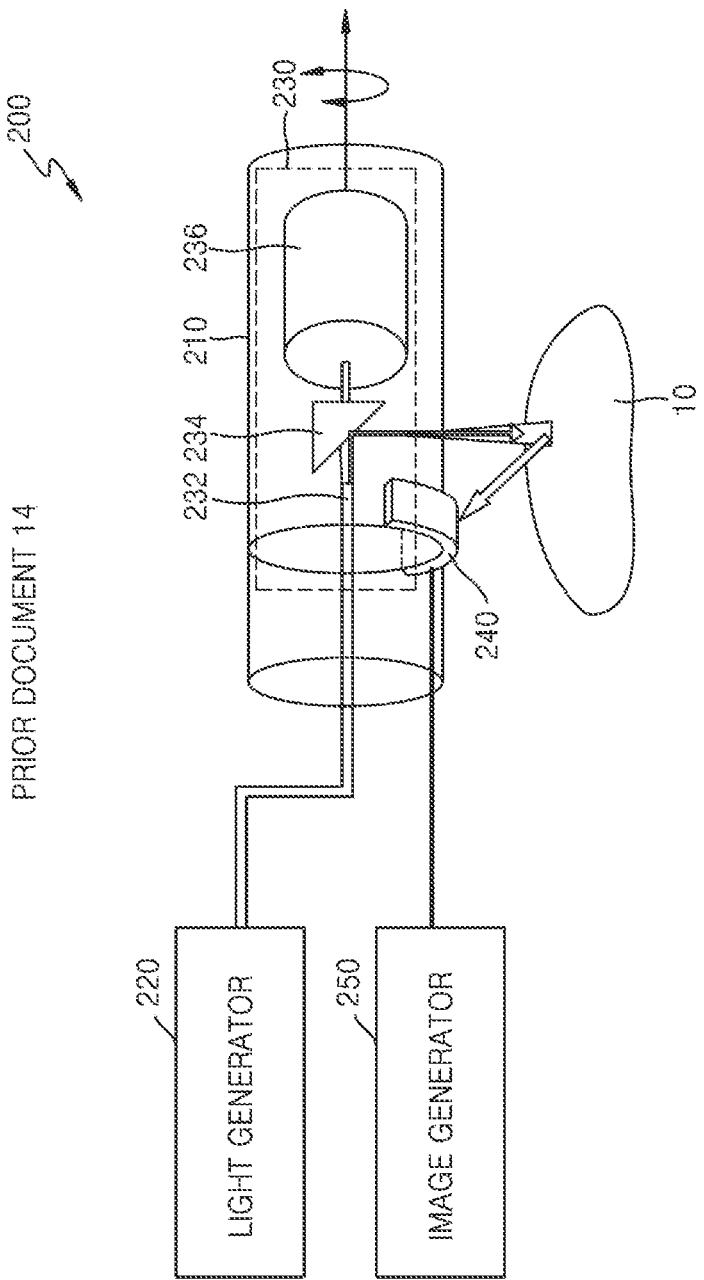

FIG. 14 is a view illustrating an exemplary embodiment of a balloon installed on an end of a PAE-EUS probe in order to solve an acoustic matching problem between an object to be examined and the endoscopic probe during an endoscopic imaging procedure. Since the current endoscopic system obtains a signal by means of ultrasonic waves (as in existing EUS systems), the same balloon contact method currently used in EUS can be applied. To this end, the scanning head 1110 may be entirely enveloped by a balloon 5000, and water may be injected into the balloon 5000 through a small fluid injection hole 1120-1 formed around the second groove for balloon fixation 1140, which is located between the scanning head base frame 1120 and the hose end frame 1130 or at any spot formed on the scanning head base frame 1120. Of course, the amount of water injected into the balloon 5000 can be controlled, which can allow the balloon 5000 to expand and adhere to the wall of a specimen.

Until now, a principle for obtaining photoacoustic-ultrasonic dual-mode 2D or 3D tomographic images using the endoscopic system provided by the present disclosure has been described. However, if necessary, proposed concepts may be implemented in such a system embodiment that only obtains partial image information (e.g., photoacoustic image only). Moreover, in the configuration and arrangement of the subsystems shown in FIG. 1, some of the elements may be integrated into a single physical unit, and the spatial positions of some of the elements may be changed appropriately. For example, the laser source 2000 could be integrated with the system console 4000, and various cables, such as the probe-console communication cable 1700, the transducer data cable 1800, and the guiding optical fiber cable 1900 that are connected to the base of the PAE-EUS probe 1000, may also be integrated into a single cable.

In the present disclosure, a detailed system concept and probe structure for solving the mismatch issue between an LEA and a USA and the limited imaging depth issue of prior inventions has been described, as have several exemplary embodiments.

In general, the main reason for utilizing such an array transducer-based electronic scanning mechanism in GI endoscopy is to achieve a large-depth imaging performance. However, prior inventions have shown a fundamental limit in terms of this performance due to the aforementioned problems. In contrast, the present disclosure could successfully solve those problems by using the light diffuser 1112 and the optically-transparent array transducer 1111 concepts; the present disclosure also presented a very detailed system structure for applying the proposed concepts to GI endoscopy, for which no other prior invention has suggested any detailed system configuration.

The main reason that the present disclosure could successfully achieve a large-depth imaging performance within a limited probe size, which has been the biggest technical challenge in the PAE field, is because the LEA and the USA of the scanning head overlap each other by employing an array transducer 1111 with optical transparency. Moreover, due to the concept, the mismatch issue between an IA and an SA of prior inventions could be solved simultaneously.

As described above, according to an embodiment, the mismatch issue between an IA and an SA of prior PAE systems may be solved, and much more light energy can be delivered than is possible with prior inventions; thus, the maximum imaging depth of a PAE system may be greatly increased up to the theoretical limit that is determined by the ANSI safety regulation (i.e., Prior Documents 16). However, the scope of the present disclosure is not limited by the effect.

While one or more embodiments have been described with reference to the figures, it will be understood by those of ordinary skill in the art that various changes in form and details may be made therein without departing from the spirit and scope of the disclosure as defined by the following claims.

What is claimed is:

1. A photoacoustic and ultrasonic endoscope comprising:
   an optical fiber;
   a light diffuser configured to diffuse a laser beam in a radial direction, the laser beam being transmitted through the optical fiber;
   an array transducer that is optically transparent, has a cylindrical shape with a curved side surface, and surrounds the light diffuser completely in the radial direction,
   wherein the light diffuser comprises:
      a mirror located at a center of the array transducer and comprising a reflective surface capable of radially reflecting the laser beam transmitted through the optical fiber; and
      a beam shaper between the mirror and the optical fiber and configured to deflect the laser beam transmitted through the optical fiber such that a traveling direction of the laser beam is changed,
   wherein the array transducer is configured to transmit the laser beam from the light diffuser through the curved side surface of the array transducer and to generate an ultrasonic wave or detect an ultrasonic wave generated by an object to be examined through the curved side surface of the array transducer.

2. The photoacoustic and ultrasonic endoscope of claim 1, wherein the laser beam diffused by the light diffuser passes through an entire area of the curved side surface of the array transducer.

3. The photoacoustic and ultrasonic endoscope of claim 1, wherein a light emitting area on an outer surface of the array transducer and an ultrasonic sensor area on the outer surface of the array transducer overlap each other, the diffused laser beam exits the array transducer through the light emitting area, and an ultrasonic wave that the array transducer senses passes through the ultrasonic sensor area.

4. The photoacoustic and ultrasonic endoscope of claim 1, further comprising an acoustic matching layer covering at least a portion of an outer surface of the array transducer, the acoustic matching layer comprising a light-transmissive material.

5. The photoacoustic and ultrasonic endoscope of claim 4, wherein the acoustic matching layer further comprises polymethylpentene (TPX).

6. The photoacoustic and ultrasonic endoscope of claim 1, wherein the beam shaper comprises an electro-optic modulator (EOM) capable of focusing the laser beam in a particular direction.

7. The photoacoustic and ultrasonic endoscope of claim 1, wherein the mirror has a cone-like shape.

8. The photoacoustic and ultrasonic endoscope of claim 1, wherein the light diffuser further comprises a cylindrical light scattering layer located inside the array transducer and surrounding the mirror.

9. The photoacoustic and ultrasonic endoscope of claim 8, wherein a reduced scattering coefficient ($\mu_s'$) of the light scattering layer is equal to or greater than $0.1$ cm$^{-1}$, and equal to or less than $1.0$ cm$^{-1}$.

10. The photoacoustic and ultrasonic endoscope of claim 1, wherein the array transducer comprises:
   a piezoelectric layer having a certain thickness;
   a plurality of first electrodes arranged on a first surface of the piezoelectric layer in a form of a one-dimensional or two-dimensional array; and
   a plurality of second electrodes on a second surface of the piezoelectric layer, the second surface facing the first surface, and the second electrodes being arranged parallel to the plurality of first electrodes.

11. The photoacoustic and ultrasonic endoscope of claim 10, further comprising an optically-transparent backing layer between the light diffuser and the piezoelectric layer.

12. The photoacoustic and ultrasonic endoscope of claim 10, wherein the first electrodes and the second electrodes are optically-transparent electrodes.

13. The photoacoustic and ultrasonic endoscope of claim 10, wherein the plurality of first electrodes and the plurality of second electrodes comprise opaque electrodes.

14. The photoacoustic and ultrasonic endoscope of claim 13, further comprising a light reflecting layer between one of the plurality of the second electrodes and the light diffuser.

15. The photoacoustic and ultrasonic endoscope of claim 1, wherein the array transducer comprises:
   a first array transducer layer comprising a ceramic or single crystal-based piezoelectric material; and
   a second array transducer layer surrounding the first array transducer layer and comprising a polymer-based piezoelectric material.

* * * * *